(12) United States Patent
Staquicini et al.

(10) Patent No.: US 8,450,278 B2
(45) Date of Patent: May 28, 2013

(54) MUC18 TARGETING PEPTIDES

(75) Inventors: Fernanda Staquicini, Houston, TX (US); Renata Pasqualini, Houston, TX (US); Wadih Arap, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/124,550

(22) PCT Filed: Oct. 15, 2009

(86) PCT No.: PCT/US2009/060858
§ 371 (c)(1),
(2), (4) Date: Sep. 28, 2011

(87) PCT Pub. No.: WO2010/045469
PCT Pub. Date: Apr. 22, 2010

(65) Prior Publication Data
US 2012/0014869 A1 Jan. 19, 2012

Related U.S. Application Data

(60) Provisional application No. 61/105,709, filed on Oct. 15, 2008.

(51) Int. Cl.
*A61K 38/02* (2006.01)
*A61K 38/08* (2006.01)

(52) U.S. Cl.
USPC .......................................... 514/19.3; 514/6.5

(58) Field of Classification Search
None
See application file for complete search history.

(56) References Cited

U.S. PATENT DOCUMENTS

| | | | | |
|---|---|---|---|---|
| 5,595,756 | A * | 1/1997 | Bally et al. | 424/450 |
| 6,924,360 | B2 | 8/2005 | Green et al. | 530/388.1 |
| 2003/0068319 | A1 | 4/2003 | Bar-Eli | 424/141.1 |

FOREIGN PATENT DOCUMENTS

| | | |
|---|---|---|
| EP | 1382615 | 1/2004 |
| WO | WO 02/077172 | 10/2002 |
| WO | WO 2004/007550 | 1/2004 |

OTHER PUBLICATIONS

Sporn, B and Suh, N, Chemoprevention of cancer, Carcinogenesis, 2000, 21, pp. 525-530.*
Auerbach. R. et al, Angiogenesis assays: Problems and pitfalls, Cancer and Metastasis Reviews, 2000, 19, pp. 167-172.*
Gura, T. Systems for Identifying New Drugs Are Often Faulty, Science, 1997, 278, pp. 1041-1042.*
Jain R. K., Barriers to Drug Delivery in Solid Tumors, Scientific American, 1994, pp. 58-65.*
Cancer Drug Design and Discovery. Neidle, Stephen, ed., Elsevier/ACademic Press, 2008, p. 427-431.*
Almeida et al., "Mouse B-1 cell-derived mononuclear phagocyte, a novel cellular component of acute non-specific inflammatory exudate," *Int. Immunol.*, 13:1193-1201, 2001.
Arap et al., "Cell surface expression of the stress response chaperone GRP78 enables tumor targeting by circulating ligands," *Cancer Cell*, 6:275-284, 2004.
Bartholomaeus et al., "Immune response to a transplantable malignant melanoma in mice," *J. Natl. Cancer Inst.*, 53:1065-1072, 1974.
Berland and Wortis, "Origins and Functions of B-1 Cells With Notes on the Role of Cd5," *Annu. Rev. Immunol.*, 20:253-300, 2002.
Bidlingmaier et al., "Identification of MCAM/CD146 as the target antigen of a human monoclonal antibody that recognizes both epithelioid and sarcomatoid types of mesothelioma," *Cancer Research*, 69(4):1570-1577, 2009.
Broder et al., "Recombinant adenovirus-transduced dendritic cell immunization in a murine model of central nervous system tumor," *Nurosurg. Focus.* 9(6):e6, 2000.
E Brito et al., "Role of distinct immune components in the radiation-induced abrogation of systemic lupus erythematosus development in mice," *Lupus*, 16:947-954, 2007.
Cardo-Vila et al., "αvβ5 Integrin-Dependent Programmed Cell Death Triggered by a Peptide Mimic of Annexin V," *Mol. Cell*, 11:1151-1162, 2003.
Coussens and Werb, "Inflammation and cancer," *Nature*, 420:860-867, 2002.
De Visser et al., "De novo carcinogenesis promoted by chronic inflammation is B lymphocyte dependent," *Cancer Cell*, 7:411-423, 2005.
Fagarasan and Honjo, "Intestinal IgA synthesis: regulation of frontline body defences," *Immunol. Rev.*, 76:205-215, 2000.
Fidler et al., "Relationship of host immune status to tumor cell arrest, distribution and survival in experimental metastasis," *Cancer*, 40(1):46-55, 1977.
Fidler and Gersten, In: *Neoplasm Immunity: Experimental and Clinical*, Crispen (Ed.), Amsterdam: Elsevier Holland, 3:3-15, 1980.
Fidler, In: *Cancer: Principles and Practice of Oncology*, DeVita (Ed.), New York: Lippencott-Raven, 1:135-152, 1997.
Giordano et al., "Biopanning and rapid analysis of selective interactive ligands," *Nat. Med.*, 7:1249-1253, 2001.
Hajitou et al., "A Hybrid Vector for Ligand-Directed Tumor Targeting and Molecular Imaging," *Cell*, 125:385-398, 2006.
Hardy and Hayakawa, "A Hybrid Vector for Ligand-Directed Tumor Targeting and Molecular Imaging," *Immunol. Rev.*, 93:53-80, 1986.
Hendrix, "Evolution: The long evolutionary reach of viruses," *Current Biol.*, 9(24):R914-R917, 1999.
International Search Report and Written Opinion, issued in International Patent Application No. PCT/US2009/060858, mailed on Jun. 24, 2010.
Jean et al., "Loss of AP-2 Results in Up-regulation of MCAM/MUC18 and an Increase in Tumor Growth and Metastasis of Human Melanoma Cells," *J. Biol. Chem.*, 273:16501-16508, 1998.
Johnson et al., In: *Biotechnology and Pharmacy*, Pezzuto (Ed.), New York, 1993.

(Continued)

*Primary Examiner* — Julie Ha
*Assistant Examiner* — Li Ni Komatsu
(74) *Attorney, Agent, or Firm* — Parker Highlander PLLC

(57) ABSTRACT

Provided are MUC 18 targeting peptides which may be used, e.g., to therapeutically target B-I lymphocytes to reduce the influence of these cells on the metastatic potential of melanoma cells and/or to target cancerous cells, including certain melanoma and leukemia cells. MUC 18 targeting peptides may be comprised in fusion constructs, imaging constructs, and/or therapeutic constructs such as fusion constructs which may be used for diagnosing or treating a cancer.

15 Claims, 6 Drawing Sheets

OTHER PUBLICATIONS

Kantor and Herzenberg, "Origin of Murine B Cell Lineages," *Annu. Rev. Immunol.*, 11:501-538, 1993.

Khan et al., "Defective B cell development and function in Btk-deficient mice," *Immunity*, 3:283-299, 1995.

Kolonin et al., "Reversal of obesity by targeted ablation of adipose tissue," *Nat. Med.*, 10:625-632, 2004.

Lehmann et al., "MUC18, a marker of tumor progression in human melanoma, shows sequence similarity to the neural cell adhesion molecules of the immunoglobulin superfamily," *Proc. Natl. Acad. Sci. USA*, 86(24):9891-9895, 1989.

Leslie et al., "Immunization against MUC18/MCAM, a novel antigen that drives melanoma invasion and metastasis," *Gene Ther.*, 14(4):316-323, 2007.

Luca et al., "Direct correlation between MUC18 expression and metastatic potential of human melanoma cells," *Melanoma Res.*, 3:35-41, 1993.

Marchio et al., "Aminopeptidase A is a functional target in angiogenic blood vessels," *Cancer Cell*, 5:151-162, 2004.

Pasqualini and Ruoslahti, "Organ targeting in vivo using phage display peptide libraries," *Nature*, 380:364-366, 1996.

Pasqualini et al., "Aminopeptidase N is a Receptor for Tumor-homing Peptides and a Target for Inhibiting Angiogenesis," *Cancer Res.*, 60:722-727, 2000.

Perez et al, "B-1 lymphocytes increase metastatic behavior of melanoma cells through the extracellular signal-regulated kinase pathway," *Cancer Sci.*, 99:920-928, 2008.

Popi et al., "Interleukin-10 secreted by B-I cells modulates the phagocytic activity of murine macrophages in vitro," *Immunology*, 113:348-354, 2004.

Prehn, "The Immune Reaction as a Stimulator of Tumor Growth," *Science*, 176:170-171, 1982.

Santos-Lima et al., "Significant association between the skewed natural antibody repertoire of Xid mice and resistance to Trypanosoma cruzi infection," *Eur. J. Immonol.*, 31:634-645, 2001.

Shih, "The role of CD146 (Mel-CAM) in biology and pathology," *J. Pathol.*, 189:4-11, 1999.

Staquicini et al., "A subset of host B lymphocytes controls melanoma metastasis through a melanoma cell adhesion molecule/MUC18-dependent interaction: evidence from mice and humans," *Cancer Res.*, 68(20):8419-8428, 2008.

Yang et al., "Isolation and characterization of mouse MUC18 cDNA gene, and correlation of MUC18 expression in mouse melanoma cell lines with metastatic ability," *Gene*, 265:133-145, 2001.

\* cited by examiner

SEQUENCE LISTING

```
<160> NUMBER OF SEQ ID NOS: 22

<210> SEQ ID NO 1
<211> LENGTH: 9
<212> TYPE: PRT
<213> ORGANISM: Artificial
<220> FEATURE:
<223> OTHER INFORMATION: Synthetic peptide

<400> SEQUENCE: 1

Cys Leu Phe Met Arg Leu Ala Trp Cys
1               5

<210> SEQ ID NO 2
<211> LENGTH: 10
<212> TYPE: PRT
<213> ORGANISM: Artificial
<220> FEATURE:
<223> OTHER INFORMATION: Synthetic peptide

<400> SEQUENCE: 2

His Asp Glu Arg Met Phe Leu Cys Lys Ser
1               5                   10

<210> SEQ ID NO 3
<211> LENGTH: 14
<212> TYPE: PRT
<213> ORGANISM: Artificial
<220> FEATURE:
<223> OTHER INFORMATION: Synthetic peptide

<400> SEQUENCE: 3

Lys Leu Ala Lys Leu Ala Lys Lys Leu Ala Lys Leu Ala Lys
1               5                   10

<210> SEQ ID NO 4
<211> LENGTH: 27
<212> TYPE: DNA
<213> ORGANISM: Artificial
<220> FEATURE:
<223> OTHER INFORMATION: Synthetic primer

<400> SEQUENCE: 4
ggatccttgg cttgcgccct ccgtcgg                                    27
```

<210> SEQ ID NO 5
<211> LENGTH: 30
<212> TYPE: DNA
<213> ORGANISM: Artificial
<220> FEATURE:
<223> OTHER INFORMATION: Synthetic primer

<400> SEQUENCE: 5
ctaatgcctc agatcgatgt atttctctcc                                       30

<210> SEQ ID NO 6
<211> LENGTH: 20
<212> TYPE: DNA
<213> ORGANISM: Artificial
<220> FEATURE:
<223> OTHER INFORMATION: Synthetic primer

<400> SEQUENCE: 6
cgcctggtca ccagggctgc                                                  20

<210> SEQ ID NO 7
<211> LENGTH: 21
<212> TYPE: DNA
<213> ORGANISM: Artificial
<220> FEATURE:
<223> OTHER INFORMATION: Synthetic primer

<400> SEQUENCE: 7
caccaccctg ttgctgtagc c                                                21

<210> SEQ ID NO 8
<211> LENGTH: 19
<212> TYPE: DNA
<213> ORGANISM: Artificial
<220> FEATURE:
<223> OTHER INFORMATION: Synthetic primer

<400> SEQUENCE: 8
ggagagaaat acatcgatc                                                   19

<210> SEQ ID NO 9
<211> LENGTH: 19
<212> TYPE: DNA
<213> ORGANISM: Artificial
<220> FEATURE:
<223> OTHER INFORMATION: Synthetic primer

<400> SEQUENCE: 9
gatcgatgta tttctctcc                                                   19

<210> SEQ ID NO 10
<211> LENGTH: 19
<212> TYPE: DNA
<213> ORGANISM: Artificial
<220> FEATURE:
<223> OTHER INFORMATION: Synthetic primer

<400> SEQUENCE: 10
taaggctatg aagagatac                                                   19

<210> SEQ ID NO 11
<211> LENGTH: 19
<212> TYPE: DNA
<213> ORGANISM: Artificial
<220> FEATURE:
<223> OTHER INFORMATION: Synthetic primer

```
<400> SEQUENCE: 11
gtatctcttc atagcctta                                               19

<210> SEQ ID NO 12
<211> LENGTH: 4
<212> TYPE: PRT
<213> ORGANISM: Artificial
<220> FEATURE:
<223> OTHER INFORMATION: Synthetic peptide

<400> SEQUENCE: 12

Arg Met Phe Leu
1

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Cys Phe Arg Gly Ser Thr Gly Ser Cys
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Cys Leu Tyr Leu Met Gly Gln Arg Cys
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Cys Gly Pro Val Leu Trp Gly Ala Cys
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Cys Gly Ala Pro Leu Tyr Phe Ala Cys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17
```

```
Cys Leu Arg Arg Ser Gly Gly Met Cys
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Cys Phe Gln Ala Arg Val Pro Cys
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Cys Leu Val Pro Gly Val Ser Ser Cys
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Cys Val Leu Asn Arg Thr Gln Leu Cys
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Cys Asp Arg Gly Val Asn Gly Thr Cys
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

Leu Phe Met Arg Leu Ala Trp
1               5
```

MUC18 TARGETING PEPTIDES

The present application is a national phase application under 35 U.S.C. §371 of International Patent Application No. PCT/US2009/060858, filed Oct. 15, 2009, which claims priority to U.S. Application No. 61/105,709 filed on Oct. 15, 2008, the entire disclosure of each of which are specifically incorporated herein by reference in their entirety without disclaimer.

BACKGROUND OF THE INVENTION

1. Field of the Invention

The present invention relates generally to the fields of molecular biology and medicine. More particularly, it concerns MUC18-targeting peptides.

2. Description of the Related Art

Studies addressing the role of the immune system in tumor growth and metastasis have yielded conflicting and often counterintuitive results. Over the 1970's, Prehn and colleagues proposed that the immune response mediated by lymphoid cells could paradoxically lead to tumor cell stimulation (Prehn, 1971; Prehn, 1982; Wexler et al., 1976). To date, the interplay of immunity, inflammation, and cancer is still not entirely understood (Coussens and Serb, 2002; de Visser et al., 2005). To add a further level of complexity—depending on the experimental model used—it is evident that host immunity can actually lead to enhancement, suppression, or even no effect at all on the metastatic potential of tumor cells, so that no global generalizations can be easily made (Fidler, 1997).

Specifically in the B16 mouse melanoma model, previous reports demonstrate that melanoma cells can be stimulated by lymphocytes (Bartholomaeus et al., 1974) and that melanoma progression can indeed be delayed if tumor-bearing mice are rendered immunosuppressed (Fidler and Gersten, 1980). However, the basis for these intriguing experimental observations remains elusive. In particular, the relevance of cell subpopulations from the more primitive layers of the immune system such as B-1 lymphocytes (Berland and Wortis, 2002; Hardy and Hayakawa, 1986; Kantor and Herzenberg, 1993; Fagarasan et al., 2000) on tumor phenotype has not been fully elucidated, although it has been suggested that B-1 cells can physically interact with melanoma cells (Perez et al., 2008).

Although B-1 lymphocytes may contribute to the metastasis of melanoma cells, it is not clear how to therapeutically inhibit this interaction to decrease metastasis of a cancer. Part of the reason that methods for decreasing this interaction are, to the knowledge of the inventors, essentially non-existent is due to the fact that the mechanism by which these cells interact has not previously been elucidated. Clearly, there exists a need for new methods and therapeutics for the treatment of cancer.

SUMMARY OF THE INVENTION

The present invention overcomes limitations in the prior art by providing MUC18-targeting peptides which may be used, e.g., to therapeutically disrupt the interaction of and/or selectively kill B-1 lymphocytes and cancer cells, including certain melanoma cells, which express MUC18. Preventing or decreasing the interaction between B-1 lymphocytes and cancerous cells reduces the ability of B-1 lymphocytes to promote the metastasis of cancers. The inventors have discovered that the MUC18-targeting peptides may target both cancerous cells and/or blood vessels involved in vascularization. In various embodiments, it is anticipated that a MUC18-targeting peptide of the present invention (e.g., comprising SEQ ID NO:22, SEQ ID NO:1, or SEQ ID NO:2) may directly exhibit anti-tumor activity in the absence of the conjugation of a cytotoxic payload to the MUC18-targeting peptide. The MUC18 targeting peptides of the present invention may also be comprised in fusion constructs, imaging constructs, and/or therapeutic constructs and may be used, e.g., for the treatment of cancer.

The invention is based, in part, on the discovery that MUC18 (also referred to as "melanoma cell adhesion molecule" or MCAM) is critical for the ability of B-1 lymphocytes to promote the metastasis of melanoma cells. As illustrated in further detail below and in the examples, the inventors utilized phage display and other methods to generated several MUC18-targeting peptides (e.g., SEQ ID NO:22, SEQ ID NO:1, SEQ ID NO:2) which can selectively bind to both human and/or mouse cancerous cells as well as B-1 lymphocytes. Without wishing to be bound by any theory, the data presented in the examples below indicate that a MUC18-MUC18 homophilic interaction mediates the physical contact between B16 cells and B-1 lymphocytes, and this physical interaction is critical for the ability of a B-1 lymphocyte to promote the metastasis of cancer. Thus, disruption of this interaction may thus therapeutically decrease the metastasis of certain cancers. MUC18-targeting peptides, such as SEQ ID NO:22, SEQ ID NO:1, and/or SEQ ID NO:2 may comprise R- and/or L-amino acids, or amino acids which are resistant to degradation when administered to a subject in vivo.

An aspect of the present invention relates to an isolated peptide that selectively binds melanoma cell adhesion molecule (MUC18) comprising SEQ ID NO:22, SEQ ID NO:1 or SEQ ID NO:2; wherein if the peptide comprises SEQ ID NO:2, then the peptide is not MUC18. The isolated peptide may be therapeutic for the treatment of cancer, such as a leukemia or a melanoma. In certain embodiments, the peptide is from 6 to 35, or from 7 to 15, amino acids in length. The isolated peptide may be covalently or non-covalently coupled to a therapeutic agent, such as a drug, chemotherapeutic agent, radioisotope, pro-apoptosis agent, anti-angiogenic agent, hormone, cytokine, cytotoxic agent, cytocidal agent, cytostatic agent, peptide, protein, antibiotic, antibody, Fab fragment of an antibody, hormone antagonist, nucleic acid or antigen. The anti-angiogenic agent may be selected from the group consisting of thrombospondin, angiostatin, pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, Docetaxel, polyamines, a proteasome inhibitor, a kinase inhibitor, a signaling peptide, accutin, cidofovir, vincristine, bleomycin, AGM-1470, platelet factor 4, and minocycline. The pro-apoptosis agent may be selected from the group consisting of etoposide, ceramide sphingomyelin, Bax, Bid, Bik, Bad, caspase-3, caspase-8, caspase-9, fas, fas ligand, fadd, fap-1, tradd, faf, rip, reaper, apoptin, interleukin-2 converting enzyme or annexin V. The cytokine may be selected from the group consisting of interleukin 1 (IL-1), IL-2, IL-5, IL-10, IL-12, IL-18, interferon-γ (IF-γ), IF α, IF-β, tumor necrosis factor-α (TNF-α), or GM-CSF (granulocyte macrophage colony stimulating factor).

In certain embodiments, the peptide is attached to a molecular complex. The complex may be a virus, a bacteriophage, a bacterium, a liposome, a microparticle, a magnetic bead, a yeast cell, a mammalian cell or a cell. The virus may be chosen from the group consisting of adenovirus, retrovirus adeno-associated virus (AAV), and AAVP. The virus may be further defined as containing a gene therapy vector. The peptide may be attached to a eukaryotic expression vector, such as a gene therapy vector. The peptide may be comprised in a pharmaceutically acceptable composition.

Another aspect of the present invention relates to a nucleic acid that encodes a protein or peptide comprising SEQ ID NO:22, SEQ ID NO:1 or SEQ ID NO:2, wherein if the nucleic acid comprises SEQ ID NO:2, then the protein or peptide is not MUC18. In certain embodiments, the nucleic acid does not consist of a nucleic acid that encodes a full-length MUC18 protein, and the nucleic acid may encode a peptide or protein comprising less than the full-length MUC18. The nucleic acid may be operably linked to a heterologous promoter.

Yet another aspect of the present invention relates to a method of treating a hyperproliferative disease or cancer comprising administering to a subject a peptide that selectively binds MUC18. The peptide may inhibit growth of a cancer cell. The cancer may be a leukemia or a melanoma. The peptide may be selected from the group consisting of SEQ ID NO:22, SEQ ID NO:1 and SEQ ID NO:2. The subject may be a mammal, such as a human. The peptide may be administered in a pharmaceutically acceptable carrier. The method may further comprise administering a second therapeutic agent to the subject. The peptide may be coupled to a therapeutic agent. The therapeutic agent may be a drug, a chemotherapeutic agent, a radioisotope, a pro-apoptosis agent, an anti-angiogenic agent, a hormone, a cytokine, a cytotoxic agent, a cytocidal agent, a cytostatic agent, a peptide, a protein, an antibiotic, an antibody, a Fab fragment of an antibody, a hormone antagonist, a nucleic acid or an antigen. The anti-angiogenic agent may be selected from the group consisting of thrombospondin, angiostatin, pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-$\beta$, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, Docetaxel, polyamines, a proteasome inhibitor, a kinase inhibitor, a signaling peptide, accutin, cidofovir, vincristine, bleomycin, AGM-1470, platelet factor 4 and minocycline. The pro-apoptosis agent may be selected from the group consisting of etoposide, ceramide sphingomyelin, Bax, Bid, Bik, Bad, caspase-3, caspase 8, caspase-9, fas, fas ligand, fadd, fap-1, tradd, faf, rip, reaper, apoptin, interleukin-2 converting enzyme or annexin V. The cytokine may be selected from the group consisting of interleukin 1 (IL-1), IL-2, IL-5, IL-10, IL-12, IL-18, interferon-$\gamma$ (IF-$\gamma$), IF-$\alpha$, IF-$\beta$, tumor necrosis factor-$\alpha$ (TNF-$\alpha$), or GM-CSF (granulocyte macrophage colony stimulating factor).

Yet another aspect of the present invention relates to a method for imaging cells expressing MUC18 comprising exposing cells to an isolated peptide that selectively binds MUC18, wherein the peptide is coupled to a radioisotope or an imaging agent. The cells may comprise melanoma cells, leukemia cells, or blood vessel cells. The isolated peptide may comprise SEQ ID NO:22, SEQ ID NO:1 or SEQ ID NO:2.

Another aspect of the present invention relates to an isolated peptide that selectively binds MUC18, identified by a process comprising: contacting a cell or tissue expressing MUC18 with a plurality of phage, wherein each phage comprises heterologous peptide sequences incorporated into a fiber protein, removing the phage that do not bind to the cell or tissue expressing MUC18, and isolating the phage that bind the cell or tissue expressing MUC18. The process may be repeated at least twice. The process may further comprise isolating and sequencing isolated phage nucleic acid. The cell or tissue may endogenously or exogenously express MUC18.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
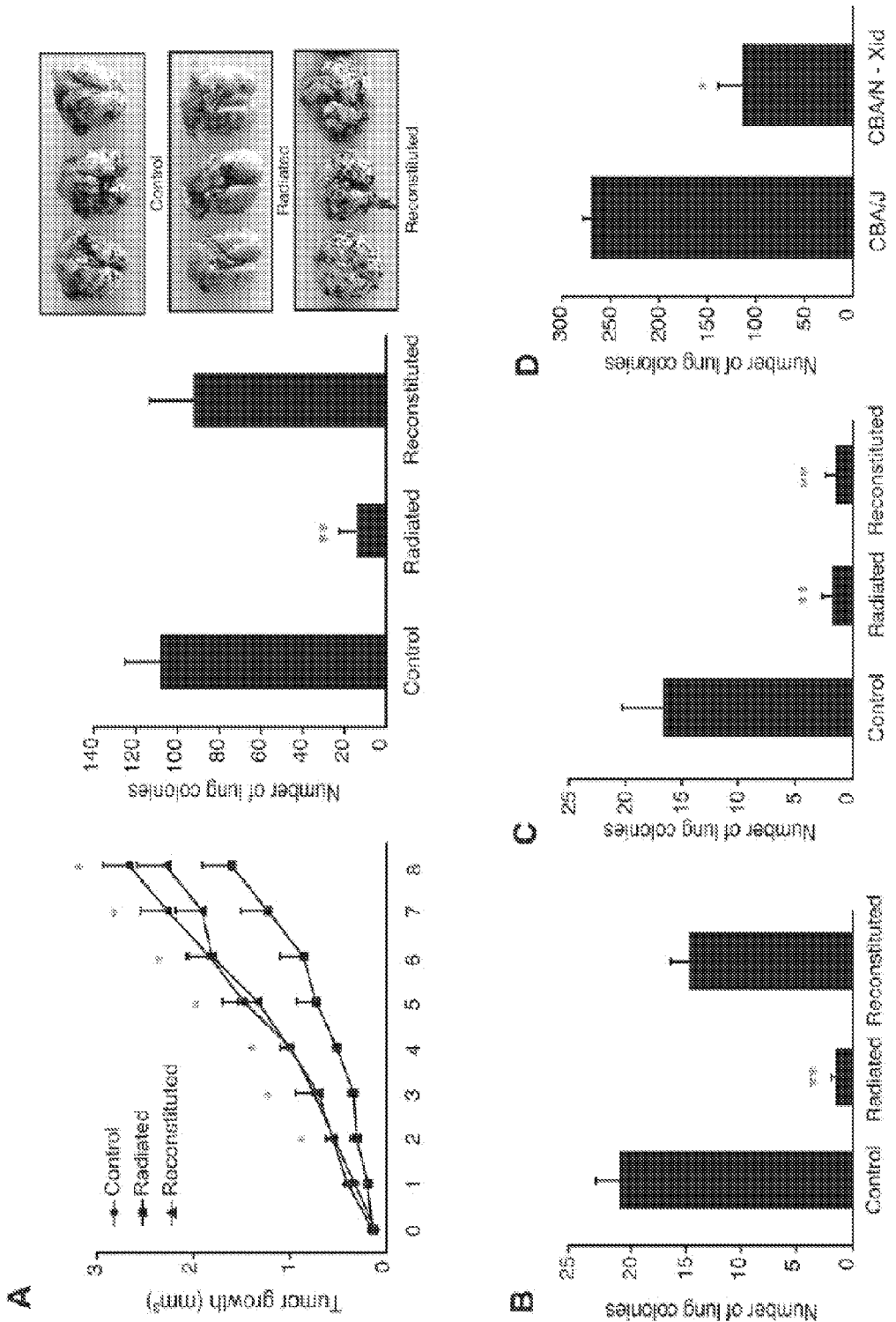
FIG. 1. Effects of B-1 lymphocytes in B16 melanoma progression. A, Left panel: effect of radiation-induced B-1 lymphocyte depletion on primary tumor growth represented in days following each treatment. Middle and Right panels: Effect of radiation-induced B-1 lymphocyte depletion on metastases. Representative lungs containing melanoma metastases from control, radiated and reconstituted mice. B and C, Effect of reconstitution with B-1 lymphocytes or other cell types on metastases. B-1 lymphocyte reconstitution (B) but not all other peritoneal cell types (C), reverts the radiation-induced metastases suppression. D, Effects of constitutive B-1 lymphocyte depletion on metastases in CBA/J and CBA/N-Xid mice. Suppression of metastases from B16 melanoma in mice with constitutive B-1 lymphocyte depletion (X-linked immunosuppression, Xid) relative to otherwise isogenic control mice (wt). *, $p<0.05$; ** $p<0.01$ FIG. 2. Screening of a phage display random peptide library on B16 melanoma cells post co-culture with B-1 lymphocytes yields MUC18 as a candidate target molecule. A, Enrichment of phage binding to malignant melanoma cells after co-culture with B-1 lymphocytes. The Y axis is set forth in terms of relative transducing units ("Relative TU"). B, Binding of individual MUC18-mimic phage clones to B16 malignant melanoma cells pre and post co-culture with B-1 lymphocytes. A phage clone displaying the peptide motif Arg-Met-Phe-Leu (mouse MUC18 residues A114-L117) had a marked increase in binding to B16 melanoma cells post co-culture with B-1 lymphocytes relative to control insertless phage (~20-fold) or to malignant melanoma cells without co-culture with B-1 lymphocytes (~12-fold). Experiments were performed three times with similar results; a representative binding experiment is shown. The Y axis is set forth in terms of relative transducing units ("Relative TU"). C, The selected CLFMRLAWC-phage (CLFMRLAWC is SEQ ID NO:1) is a mimic of MUC18. Anti-MUC18 and anti-CLFMRLAWC antibodies were used to detect MUC18 on the membrane of malignant melanoma cells pre and post co-culture by Western blot analysis. D, Both anti-CLFMRLAWC and anti-MUC18 antibodies co-immunoprecipitate MUC18.

The present invention overcomes limitations in the prior art by providing new compounds and methods for the treatment of cancer. In particular, new MUC18-targeting peptides have been produced and may be used to selectively bind with cancerous cells and B-1 lymphocytes. Without wishing to be bound by any theory, the data presented herein indicates that MUC18-MUC18 homophilic interaction is critical for the physical contact between B-1 lymphocytes and cancerous cells. Reducing this physical interaction may thus therapeutically reduce the ability of B-1 lymphocytes to promote the metastasis of a cancer or hyperproliferative cell. The MUC18-targeting peptides (e.g., SEQ ID NO:#, SEQ ID NO:1, SEQ ID NO:2) may be used therapeutically or for imaging. For example, a MUC18-targeting peptide may be conjugated to a cytotoxic moiety and used to selectively kill cancerous cells and/or B-1 lymphocytes, and, in various embodiments, a MUC18-targeting peptide may also be conjugated to an imaging moiety and used to for imaging.

As shown in the below examples, phage-display was used to identify certain peptides which target murine and human melanoma in vitro and in vivo, and the cyclic peptide CLFMRLAWC (SEQ ID NO:1) was found to selectively bind to cancerous cells. This peptide contains an embedded MUC18-like motif in reverse and specifically associated with melanoma cells. The data indicated that this peptide (SEQ ID NO:1) associated with cancerous cells and B-1 lymphocytes via binding with MUC18. The cysteines at the C- and N-termini of the peptide are an artifact of the phage display system used in the below examples. However, the presence of the terminal cysteines provide the ability to produce circular peptides through the formation of a cystine, which can have various advantages, including increased protease resistance. SEQ ID NO:22 does not comprise these cysteines, but may be present in the sequence of a cyclic peptide. For example, SEQ ID NO:22 may be present in a sequence that has been modified, e.g., using a cross-linking agent, to form a cyclic peptide. In certain embodiments, SEQ ID NO:1 and/or SEQ ID NO:22 are comprised in a cyclic peptide. Alternately, it is anticipated that a linearized peptide comprising SEQ ID NO:22 may also be used to target MUC18.

The inventors further designed and constructed a phage clone displaying the peptide HDERMFLCKS (residues H111-S120 of MUC18, SEQ ID NO:2) for use in binding assays on melanoma cells. The below data indicated that the SEQ ID NO:2 peptide associated with both human and mouse cancerous cells via MUC18 binding, and the display of the MUC18-derived (H111-S120) peptide sequence on phage promoted preferential binding to the surface of melanoma cells (2.5-fold increases were observed, and several negative controls did not display significant binding to melanoma cells). Anti-MUC18 antibodies were shown to specifically inhibit phage binding mediated by the MUC18-derived peptide H111-S120 relative to controls. Furthermore, to study the specificity of the MUC18 targeted-phage in vivo, the inventors evaluated phage homing in mice subcutaneously implanted with melanoma cells. Marked binding of MUC18 targeted-phage to tumors derived from melanoma was observed.

MUC18 and Cancer

Host immunity affects tumor metastasis, but the corresponding cellular and molecular mechanisms are not entirely clear. Here the inventors show that a subset of B-lymphocytes (termed B-1 population), in contrast to other lymphocytes, have pro-metastatic effects on melanoma cells in vivo through a direct heterotypic cell-cell interaction. In the B16 mouse melanoma model, one mechanism underlying this phenomenon is a specific upregulation and subsequent homophilic interaction mediated by the cell surface glycoprotein MUC18 (also known as melanoma cell adhesion molecule; MCAM). Presence of B-1 lymphocytes in a panel of tumor samples from melanoma patients directly correlated with MUC18 expression in melanoma cells, indicating that the same protein interaction exists in humans. These results suggest a new functional role for host B-1 lymphocytes in tumor metastasis and establish a biochemical basis for such observations. Without wishing to be bound by any theory, these findings support the counterintuitive central hypothesis in which a primitive layer of the immune system actually contributes to tumor progression and metastasis. Given that monoclonal antibodies against MUC18 are in pre-clinical development, but the reason for their anti-tumor activity is not well understood, these translational results are relevant in the setting of human melanoma, and perhaps of other cancers.

Despite the importance of bone marrow stromal cells in hematopoiesis, the profile of surface molecule expression is relatively poorly understood. Mice were immunized with cultured human bone marrow stromal cells in order to raise monoclonal antibodies to novel cell surface molecules, which might be involved in interactions with hematopoietic cells. Three antibodies, WM85, CC9 and EB4 were produced, and were found to identify a 100-110 kDa antigen on bone marrow fibroblasts. Molecular cloning revealed the molecule to be MUC18 (CD146), a member of the immunoglobulin superfamily, previously described as a marker of metastatic melanoma. In addition to the expected expression on melanoma cell lines and endothelial cells, a number of human leukemic cell lines were found to express MUC18, including all six T leukemia lines tested, one of five B lineage lines and one of four myeloid lines. Analysis of bone marrow samples from patients revealed positivity in 20% of B lineage ALL (n=20), one of three T-ALL, 15% of AML (n=13) and 43% of various B lymphoproliferative disorders (n=7). No apparent reactivity was observed with mononuclear cells from normal peripheral blood or bone marrow, including candidate hematopoietic stem cells characterized by their expression of the CD34 antigen. However, positive selection of bone marrow mononuclear cells labeled with MUC18 antibody revealed a rare subpopulation (<1%) containing more than 90% of the stromal precursors identified in fibroblast colony-forming assays. The structure and tissue distribution of MUC18 suggest a functional role in regulation of hemopoiesis.

Proteins and Peptides

MUC18-targeting peptides are provided herein. The peptides may be provided alone or comprised in a larger amino acid sequence. In certain embodiments, the present invention concerns novel compositions comprising a MUC18-targeting protein or peptide. As used herein, a protein or peptide generally refers, but is not limited to, a protein of greater than about 200 amino acids up to a full length sequence translated from a gene; a polypeptide of about 100 to 200 amino acids; and/or a peptide of from about 3 to about 100 amino acids. For convenience, the terms "protein," "polypeptide" and "peptide" are used interchangeably herein.

In certain embodiments the size of at least one protein or peptide may comprise, but is not limited to, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 or greater amino acid residues, or any range derivable therein. In certain embodiments, a peptide that targets MUC18 may comprise from 6 to 35, 7 to 35, 9 to 25, or from 7 to 15 amino acids. A peptide targeting MUC18 may be conjugated to a second agent, such as a therapeutic agent, or the peptide may be conjugated to additional amino acids.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown on Table 2 below.

TABLE 2

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Proteins or peptides may be made by any technique known to those of skill in the art, including the expression of proteins, polypeptides, or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases (world wide web at nlm.nih.gov/). The coding regions for known genes may be amplified and/or expressed using the techniques disclosed herein or as would be know to those of ordinary skill in the art. Alternatively, various commercial preparations of proteins, polypeptides and peptides are known to those of skill in the art.

Peptide Mimetics

Peptide mimetics may be produced, e.g., based on the MUC18-targeting peptides. Mimetics are peptide-containing molecules that mimic elements of protein secondary structure. See, for example, Johnson et al., (1993), incorporated herein by reference. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting peptides disclosed herein, but with altered and even improved characteristics.

Fusion Proteins

MUC18-targeting peptides may be expressed as fusion proteins. Fusion proteins generally have all or a substantial portion of a targeting peptide, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. In preferred embodiments, the fusion proteins of the instant invention comprise a targeting peptide linked to a therapeutic protein or peptide. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually and protein or peptide could be incorporated into a fusion protein comprising a targeting peptide. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

Protein Purification

Methods for the isolation and/or purification of a protein or peptide are known in the art and may be used, e.g., to produce MUC18-targeting peptides. In one embodiment, an MUC18-targeting proteins or peptide may be used to generate antibodies for tagging with any of the illustrated barcodes (e.g. polymeric Raman label). Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide include ion-exchange chromatography, gel exclusion chromatography, HPLC (high performance liquid chromatography) FPLC (AP Biotech), polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. One of the more efficient methods of purifying peptides is fast performance liquid chromatography (AKTA FPLC). A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and/or combinations of these or other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in its most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

Synthetic Peptides

Because of their relatively small size, certain MUC18-targeting peptides can be synthesized in solution or on a solid support in accordance with conventional techniques. Synthesis of peptides, e.g., less than 40 amino acids long, can provide the advantage of avoiding the use of animal products; this may be particularly useful when it is desired to administer the MUC18-targeting peptide to a human. Various automatic synthesizers are commercially available and can be used in accordance with known protocols. See, for example, Stewart and Young, 1984; Tam et al., 1983; Merrifield, 1986; and Barany and Merrifield, 1979, each incorporated herein by reference. Short peptide sequences, typically up to about 35 to 50 amino acids in length, can be readily synthesized by such methods. Alternatively, recombinant DNA technology may be employed wherein a nucleotide sequence which encodes a peptide of the invention is inserted into an expression vector, transformed or transfected into an appropriate host cell, and cultivated under conditions suitable for expression.

Antibodies

In certain embodiments, it may be desirable to make antibodies against a MUC18-targeting peptide or the MUC18 receptor. The appropriate targeting peptide or receptor, or portions thereof, may be coupled, bonded, bound, conjugated, or chemically-linked to one or more agents via linkers, polylinkers, or derivatized amino acids. This may be performed such that a bispecific or multivalent composition or vaccine is produced. It is further envisioned that the methods used in the preparation of these compositions are familiar to those of skill in the art and should be suitable for administration to humans, i.e., pharmaceutically acceptable. Preferred agents are the carriers are keyhole limpet hemocyanin (KLH) or bovine serum albumin (BSA).

The term "antibody" is used to refer to any antibody-like molecule that has an antigen binding region, and includes antibody fragments such as Fab', Fab, $F(ab')_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Harlow and Lane, 1988; incorporated herein by reference).

In various embodiments of the invention, circulating antibodies from one or more individuals with a disease state may be obtained and screened against phage display libraries. Targeting peptides that bind to the circulating antibodies may act as mimeotopes of a native antigen, such as a receptor protein located on an endothelial cell surface of a target tissue. For example, circulating antibodies in an individual with prostate cancer may bind to antigens specifically or selectively localized in prostate tumors. As discussed in more detail below, targeting peptides against such antibodies may be identified by phage display. Such targeting peptides may be used to identify the native antigen recognized by the antibodies, for example by using known techniques such as immunoaffinity purification, Western blotting, electrophoresis followed by band excision and protein/peptide sequencing and/or computerized homology searches. The skilled artisan will realize that antibodies against disease specific or selective antigens may be of use for various applications, such as detection, diagnosis and/or prognosis of a disease state, imaging of diseased tissues and/or targeted delivery of therapeutic agents.

Imaging Agents and Radioisotopes

In certain embodiments, a MUC18-targeting peptide may be attached to an imaging agent and used for imaging and/or diagnosis of various diseased organs, tissues or cell types. For example, a prostate cancer selective targeting peptide may be attached to an imaging agent, provided to a subject and the precise boundaries of the cancer tissue may be determined by standard imaging techniques, such as CT scanning, MRI, PET scanning, etc. Alternatively, the presence or absence and location in the body of metastatic prostate cancer may be determined by imaging using one or more targeting peptides that are selective for metastatic prostate cancer. Targeting peptides that bind to normal as well as cancerous prostate tissues may still be of use, as such peptides would not be expected to be selectively localized anywhere besides the prostate in disease-free individuals. Naturally, the distribution of a prostate or prostate cancer selective targeting peptide may be compared to the distribution of one or more non-selective peptides to provide even greater discrimination for detection and/or localization of diseased tissues.

Many imaging agents which may be conjugated to a MUC18-targeting peptide are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509). Proteins or peptides also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, $^{14}$-carbon, $^{51}$chromium, $^{36}$-chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled proteins or peptides of the present invention may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides according to the invention may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCl$_2$, a buffer solution such as sodium-potassium phthalate solution, and the peptide. Intermediary functional groups that are often used to bind radioisotopes that exist as metallic ions to peptides are diethylenetriaminepenta-acetic acid (DTPA) and ethylene diaminetetra-acetic acid (EDTA). Also contemplated for use are fluorescent labels, including rhodamine, fluorescein isothiocyanate and renographin.

In certain embodiments, a MUC18-targeting peptides may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

Cross-Linkers

A MCU18-targeting peptide may be attached to surfaces or to therapeutic agents and/or other molecules via a cross-linking agent. Methods for covalent or non-covalent attachment of proteins or peptides are well known in the art. Such methods may include, but are not limited to, use of chemical cross-linkers, photoactivated cross-linkers and/or bifunctional cross-linking reagents. Exemplary methods for cross-linking molecules are disclosed in U.S. Pat. Nos. 5,603,872 and 5,401,511, incorporated herein by reference. Non-limiting examples of cross-linking reagents of potential use include glutaraldehyde, bifunctional oxirane, ethylene glycol diglycidyl ether, carbodiimides such as 1-ethyl-3-(3-dimethylaminopropyl) carbodiimide or dicyclohexylcarbodiimide, bisimidates, dinitrobenzene, N-hydroxysuccinimide ester of suberic acid, disuccinimidyl tartarate, dimethyl-3,3'-dithio-bispropionimidate, azidoglyoxal, N-succinimidyl-3-(2-pyridyldithio)propionate and 4-(bromoadminoethyl)-2-nitrophenylazide.

Homobifunctional reagents that carry two identical functional groups are typically highly efficient in inducing cross-linking. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied.

In certain embodiments, it may be appropriate to link one or more MUC18-targeting peptides to a liposome or other membrane-bounded particle. For example, targeting peptides cross-linked to liposomes, microspheres or other such devices may be used to deliver larger volumes of a therapeutic agent to a target organ, tissue or cell type. Various ligands can be covalently bound to liposomal surfaces through the cross-linking of amine residues. Liposomes containing phosphatidylethanolamine (PE) may be prepared by established procedures. The inclusion of PE provides an active functional amine residue on the liposomal surface.

In another non-limiting example, heterobifunctional cross-linking reagents and methods of use are disclosed in U.S. Pat. No. 5,889,155, incorporated herein by reference. The cross-linking reagents combine a nucleophilic hydrazide residue with an electrophilic maleimide residue, allowing coupling in one example, of aldehydes to free thiols. The cross-linking reagent can be modified to cross-link various functional groups.

Other techniques of general use for proteins or peptides that are known in the art have not been specifically disclosed herein, but may be used in the practice of the claimed subject matter.

Nucleic Acids

In certain embodiments, nucleic acids may encode a MUC18-targeting peptide, a receptor protein, a fusion protein or other protein or peptide. The nucleic acid may be derived from genomic DNA, complementary DNA (cDNA) or synthetic DNA. Where incorporation into an expression vector is desired, the nucleic acid may also comprise a natural intron or an intron derived from another gene. Such engineered molecules are sometime referred to as "mini-genes." In various embodiments of the invention, targeting peptides may be incorporated into gene therapy vectors via nucleic acids.

A "nucleic acid" as used herein includes single-stranded and double-stranded molecules, as well as DNA, RNA, chemically modified nucleic acids and nucleic acid analogs. It is contemplated that a nucleic acid within the scope of the present invention may be of almost any size, determined in part by the length of the encoded protein or peptide.

It is contemplated that targeting peptides, fusion proteins and receptors may be encoded by any nucleic acid sequence that encodes the appropriate amino acid sequence. The design and production of nucleic acids encoding a desired amino acid sequence is well known to those of skill in the art, using standardized codon tables. In preferred embodiments, the codons selected for encoding each amino acid may be modified to optimize expression of the nucleic acid in the host cell of interest. Codon preferences for various species of host cell are well known in the art.

In addition to nucleic acids encoding the desired peptide or protein, the present invention encompasses complementary nucleic acids that hybridize under high stringency conditions with such coding nucleic acid sequences. High stringency conditions for nucleic acid hybridization are well known in the art. For example, conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleotide content of the target sequence(s), the charge composition of the nucleic acid(s), and to the presence or concentration of formamide, tetramethylammonium chloride or other solvent(s) in a hybridization mixture.

Nucleic acids for use in the disclosed methods and compositions may be produced by any method known in the art, such as chemical synthesis (e.g. Applied Biosystems Model 3900, Foster City, Calif.), purchase from commercial sources (e.g. Midland Certified Reagents, Midland, Tex.) and/or standard gene cloning methods. A number of nucleic acid vectors, such as expression vectors and/or gene therapy vectors, may be commercially obtained (e.g., American Type Culture Collection, Rockville, Md.; Promega Corp., Madison, Wis.; Stratagene, La Jolla, Calif.).

Vectors for Cloning, Gene Transfer and Expression

In certain embodiments expression vectors are employed to express the MUC18-targeting peptide or fusion protein, which can then be purified and used. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are known.

Regulatory Elements

The terms "expression construct" or "expression vector" are meant to include any type of genetic construct containing a nucleic acid coding for a gene product in which part or all of the nucleic acid coding sequence is capable of being transcribed. In preferred embodiments, the nucleic acid encoding a gene product is under transcriptional control of a promoter. A "promoter" refers to a DNA sequence recognized by the synthetic machinery of the cell, or introduced synthetic machinery, required for initiating the specific transcription of a gene. The phrase "under transcriptional control" means that the promoter is in the correct location and orientation in relation to the nucleic acid to control RNA polymerase initiation and expression of the gene.

In various embodiments, the human cytomegalovirus (CMV) immediate early gene promoter, the SV40 early promoter, the Rouse sarcoma virus long terminal repeat, rat insulin promoter, and glyceraldehyde-3-phosphate dehydrogenase promoter can be used to obtain high-level expression of the coding sequence of interest. The use of other viral or mammalian cellular or bacterial phage promoters that are known in the art to achieve expression of a coding sequence of interest is contemplated as well, provided that the levels of expression are sufficient for a given purpose.

Where a cDNA insert is employed, one will typically include a polyadenylation signal to effect proper polyadenylation of the gene transcript. The nature of the polyadenylation signal is not believed to be crucial to the successful practice of the invention, and any such sequence may be employed, such as human growth hormone and SV40 polyadenylation signals. Also contemplated as an element of the expression construct is a terminator. These elements can serve to enhance message levels and to minimize read through from the construct into other sequences.

Selectable Markers

In certain embodiments of the invention, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin, and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome, and express viral genes stably and efficiently have made them attractive candidates for the transfer of foreign genes into mammalian cells (Ridgeway, 1988; Nicolas and Rubinstein, 1988; Baichwal and Sugden, 1986; Temin, 1986). Preferred gene therapy vectors are generally viral vectors.

In using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

DNA viruses used as gene vectors include the papovaviruses (e.g., simian virus 40, bovine papilloma virus, and polyoma) (Ridgeway, 1988; Baichwal and Sugden, 1986) and adenoviruses (Ridgeway, 1988; Baichwal and Sugden, 1986).

An exemplary method for in vivo delivery involves the use of an adenovirus expression vector. Although adenovirus vectors have a low capacity for integration into genomic DNA, this feature is counterbalanced by the high efficiency of gene transfer afforded by these vectors. "Adenovirus expression vector" is meant to include, but is not limited to, constructs containing adenovirus sequences sufficient to (a) support packaging of the construct and (b) to express an antisense or a sense polynucleotide that has been cloned therein.

Generation and propagation of adenovirus vectors that are replication deficient depend on a helper cell line, such as the 293 cell line, which was transformed from human embryonic kidney cells by Ad5 DNA fragments and constitutively expresses E1 proteins (Graham et al., 1977). Since the E3 region is dispensable from the adenovirus genome (Jones and Shenk, 1978), adenovirus vectors, with the help of 293 cells, carry foreign DNA in either the E1, the E3, or both regions (Graham and Prevec, 1991).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. Racher et al., (1995) disclosed methods for culturing 293 cells and propagating adenovirus.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993). In preferred embodiments, gene therapy vectors are based upon adeno-associated virus (AAV).

Other gene transfer vectors may be constructed from retroviruses. (Coffin, 1990.) The retroviral genome contains three genes, gag, pol, and env. that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences, and also are required for integration in the host cell genome (Coffin, 1990).

In order to construct a retroviral vector, a nucleic acid encoding protein of interest is inserted into the viral genome in the place of certain viral sequences to produce a virus that is replication-defective. In order to produce virions, a packaging cell line containing the gag, pol, and env genes, but without the LTR and packaging components, is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are capable of infecting a broad variety of cell types. However, integration and stable expression require the division of host cells (Paskind et al., 1975).

Other viral vectors may be employed as expression constructs. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984), and herpes viruses may be employed. They offer several attractive features for various mammalian cells (Friedmann, 1989; Ridgeway, 1988; Baichwal and Sugden, 1986; Coupar et al., 1988; Horwich et al., 1990).

Several non-viral methods for the transfer of expression constructs into cultured mammalian cells also are contemplated. These include calcium phosphate precipitation (Graham and van der Eb, 1973; Chen and Okayama, 1987; Rippe et al., 1990; DEAE dextran (Gopal, et al. 1985), electroporation (Tur-Kaspa et al., 1986; Potter et al., 1984), direct microinjection, DNA-loaded liposomes and lipofectamine-DNA complexes, cell sonication, gene bombardment using high velocity microprojectiles, and receptor-mediated transfection (Wu and Wu, 1987; Wu and Wu, 1988). Some of these techniques may be successfully adapted for in vivo or ex vivo use.

In a further embodiment of the invention, the expression construct may be entrapped in a liposome. Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa, and hepatoma cells. Nicolau et al., (1987) accomplished successful liposome-mediated gene transfer in rats after intravenous injection.

Pharmaceutical Compositions

Where clinical applications are contemplated, it may be necessary to prepare a pharmaceutical composition (e.g., expression vector, virus stock, protein, antibody, drug, etc.) in a form appropriate for the intended application. Generally, this will entail preparing compositions that are essentially free of impurities that could be harmful to humans or animals.

Appropriate salts and buffers may be employed to render delivery vectors stable and allow for uptake by target cells. Aqueous compositions of the present invention may comprise an effective amount of a protein, peptide, fusion protein, recombinant phage and/or expression vector, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the proteins or peptides of the present invention, its use in therapeutic compositions is contemplated. Supplementary active ingredients also can be incorporated into the compositions.

The active compositions of the present invention may include classic pharmaceutical preparations. Administration of these compositions according to the present invention are via any common route so long as the target tissue is available via that route. This includes oral, nasal, buccal, rectal, vaginal or topical. Alternatively, administration may be by orthotopic, intradermal, subcutaneous, intramuscular, intraperitoneal, intratumoral, intraarterial or intravenous injection. Such compositions normally would be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Therapeutic Agents

In certain embodiments, one or more therapeutic agent may be attached to a MUC18-targeting peptide or fusion protein for selective delivery to, for example, non-metastatic and/or metastatic prostate cancer. Agents or factors suitable for use may include any chemical compound that induces apoptosis, cell death, cell stasis and/or anti-angiogenesis or otherwise affects or decreases the survival and/or growth rate of a cancer cell.

Regulators of Programmed Cell Death

Therapeutic agents include compounds which promote apoptosis, or programmed cell death. Apoptosis is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Tsujimoto et al., 1985). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins that share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

Non-limiting examples of pro-apoptosis agents contemplated within the scope of the present invention include gramicidin, magainin, mellitin, defensin, cecropin, $(KLAKLAK)_2$ (SEQ ID NO:3).

Angiogenic Inhibitors

Therapeutic agents also include inhibitors of angiogenesis. In certain embodiments the present invention may concern administration of targeting peptides attached to anti-angiogenic agents, such as angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline.

Proliferation of tumors cells relies heavily on extensive tumor vascularization, which accompanies cancer progression. Thus, inhibition of new blood vessel formation with anti-angiogenic agents and targeted destruction of existing blood vessels have been introduced as an effective and relatively non-toxic approach to tumor treatment. (Arap et al., 1998a; 1998b; Ellerby et al., 1999). A variety of anti-angiogenic agents and/or blood vessel inhibitors are known. (e.g., Folkman, 1997; Eliceiri and Cheresh, 2001).

Cytotoxic Agents

Cytotoxic agents, such as certain chemotherapeutics, may also be conjugated to a MUC18-targeting peptide. A wide variety of anticancer agents are well known in the art and any such agent may be coupled to a MUC18-targeting peptide, and used, e.g., to treat a cancer or hyperproliferative disease in a subject (e.g., a human, mouse, rat, rodent, or primate). Exemplary cancer chemotherapeutic (cytotoxic) agents of potential use include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. Most chemotherapeutic agents fall into the categories of alkylating agents, antimetabolites, antitumor antibiotics, corticosteroid hormones, mitotic inhibitors, and nitrosoureas, hormone agents, miscellaneous agents, and any analog or derivative variant thereof.

Chemotherapeutic agents and methods of administration, dosages, etc. are well known to those of skill in the art (see for example, the "Physicians Desk Reference", Goodman & Gilman's "The Pharmacological Basis of Therapeutics" and "Remington: The Science and Practice of Pharmacy," 20th edition, Gennaro, Lippincott, 2000, each incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject. Of course, all of these dosages and agents described herein are exemplary rather than limiting, and other doses or agents may be used by a skilled artisan for a specific patient or application. Any dosage in-between these points, or range derivable therein is also expected to be of use in the invention.

Alkylating Agents

Cytotoxic agents include alkylating agents. Alkylating agents are drugs that directly interact with genomic DNA to prevent cells from proliferating. This category of chemotherapeutic drugs represents agents that affect all phases of the cell cycle, that is, they are not phase-specific. An alkylating agent, may include, but is not limited to, nitrogen mustard, ethylenimene, methylmelamine, alkyl sulfonate, nitrosourea or triazines. They include but are not limited to: busulfan, chlorambucil, cisplatin, cyclophosphamide (cytoxan), dacarbazine, ifosfamide, mechlorethamine (mustargen), and melphalan.

Antimetabolites

Antimetabolites are another example of cytotoxic agents. Antimetabolites disrupt DNA and RNA synthesis. Unlike alkylating agents, they specifically influence the cell cycle during S phase. Antimetabolites can be differentiated into various categories, such as folic acid analogs, pyrimidine analogs and purine analogs and related inhibitory compounds. Antimetabolites include but are not limited to, 5-fluorouracil (5-FU), cytarabine (Ara-C), fludarabine, gemcitabine, and methotrexate.

Natural Products

Cytotoxic agents also include certain natural agents. Natural products generally refer to compounds originally isolated from a natural source (e.g., herbal compositions), and identified as having a pharmacological activity. Such compounds, analogs and derivatives thereof may be, isolated from a natural source, chemically synthesized or recombinantly produced by any technique known to those of skill in the art. Natural products include such categories as mitotic inhibitors, antitumor antibiotics, enzymes and biological response modifiers.

Mitotic inhibitors include plant alkaloids and other natural agents that can inhibit either protein synthesis required for cell division or mitosis. They operate during a specific phase during the cell cycle. Mitotic inhibitors include, for example, docetaxel, etoposide (VP16), teniposide, paclitaxel, taxol, vinblastine, vincristine, and vinorelbine.

Taxoids are a class of related compounds isolated from the bark of the ash tree, *Taxus brevifolia*. Taxoids include but are not limited to compounds such as docetaxel and paclitaxel. Paclitaxel binds to tubulin (at a site distinct from that used by the vinca alkaloids) and promotes the assembly of microtubules.

Antibiotics

Certain antibiotics have both antimicrobial and cytotoxic activity. These drugs also interfere with DNA by chemically inhibiting enzymes and mitosis or altering cellular membranes. These agents are not phase specific so they work in all phases of the cell cycle. Examples of cytotoxic antibiotics include, but are not limited to, bleomycin, dactinomycin, daunorubicin, doxorubicin (Adriamycin), plicamycin (mithramycin) and idarubicin.

Miscellaneous Agents

Miscellaneous cytotoxic agents that do not fall into the previous categories include, but are not limited to, platinum coordination complexes, anthracenediones, substituted ureas, methyl hydrazine derivatives, amsacrine, L-asparaginase, and tretinoin. Platinum coordination complexes include such compounds as carboplatin and cisplatin (cis-DDP). An exemplary anthracenedione is mitoxantrone. An exemplary substituted urea is hydroxyurea. An exemplary methyl hydrazine derivative is procarbazine (N-methylhydrazine, MIH). These examples are not limiting and it is contemplated that any known cytotoxic, cytostatic or cytocidal agent may be attached to targeting peptides and administered to a targeted organ, tissue or cell type within the scope of the invention.

Cytokines and Chemokines

In certain embodiments, it may be desirable to couple a cytokine and/or chemokine to a MUC18-targeting peptide. The term "cytokine" is a generic term for proteins released by one cell population that act on another cell as intercellular mediators. Examples of cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-alpha. and -beta; mullerian-inhibiting substance; mouse gonadotropin-associated peptide; inhibin; activin; vascular endothelial growth factor; integrin; thrombopoietin (TPO); nerve growth factors such as NGF-.beta.; platelet-growth factor; transforming growth factors (TGFs) such as TGF-.alpha. and TGF-.beta.; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1.alpha., IL-2, IL-3, IL-4, IL-5, IL-6, IL-7, IL-8, IL-9, IL-10, IL-11, IL-12; IL-13, IL-14, IL-15, IL-16, IL-17, IL-18, LIF, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines Dosages It is anticipated that a wide variety of dosages may be used when administering a MUC18-targeting peptide to a subject (e.g., see *Remington: The Science and Practice of Pharmacy*, 2000). It is anticipated that some variation in dosage will necessarily occur depending on the condition of the subject being treated. The person responsible for administration will, in any event, determine the appropriate dose for the individual subject. Moreover, for human administration, preparations should generally meet the sterility, pyrogenicity, and general safety and purity standards as required by the FDA Office of Biologics.

Screening Phage Libraries by PALM

In certain embodiments, it is desirable to be able to select specific cell types from a heterogeneous sample of an organ or tissue. One method to accomplish such selective sampling is by PALM (Positioning and Ablation with Laser Microbeams).

The PALM Robot-Microbeam uses a precise, computer-guided laser for microablation. A pulsed ultra-violet (UV) laser is interfaced into a microscope and focused through an objective to a beam spot size of less than 1 micrometer in diameter. The principle of laser cutting is a locally restricted ablative photodecomposition process without heating (Hendrix, 1999). The effective laser energy is concentrated on the minute focal spot only and most biological objects are transparent for the applied laser wavelength. This system appears to be the tool of choice for recovery of homogeneous cell populations or even single cells or subcellular structures for subsequent phage recovery. Tissue samples may be retrieved by circumcising a selected zone or a single cell after phage administration to the subject. A clear-cut gap between selected and non-selected area is typically obtained. The isolated tissue specimen can be ejected from the object plane and catapulted directly into the cap of a common micro centrifuge tube in an entirely non-contact manner. The basics of this so called Laser Pressure Catapulting (LPC) method is believed to be the laser pressure force that develops under the specimen, caused by the extremely high photon density of the precisely focused laser microbeam. This tissue harvesting technique allows the phage to survive the microdissection procedure and be rescued.

PALM was used in the below example to select targeting phage for mouse pancreatic tissue, as described below.

Kits

In still further embodiments, the present invention concerns kits for use with the therapeutic and diagnostic methods described above. The kits generally will comprise a MUC18-targeting peptide, optionally conjugated to a therapeutic or imaging moiety, in a container means. The MUC18-targeting peptide may conjugated to a therapeutic agent and comprised in a pharmaceutical preparation in a container means. Alternately, the MUC18-targeting peptide may be conjugated to an imaging agent and comprised in a container means. Immunodetection kits may also be used to purify, quantify, or detect cells, such as cancer cells or B1-lymphocytes, which express MUC18. The immunodetection kits may comprise, in suitable container means, a protein or peptide or a nucleic acid encoding such, or a first antibody that binds to an encoded protein or peptide, and an immunodetection reagent. In certain embodiments, the protein or peptide, or the first antibody that binds to the encoded protein or peptide, may be bound to a solid support, such as a column matrix or well of a microtiter plate.

Immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of the encoded protein or peptide, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the peptide, peptide conjugate, antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

I. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A Subset of Host B-Lymphocytes Control Melanoma Metastasis Through a MCAM/MUC18-Dependent Interaction: Evidence from Mice and Humans Materials and Methods.

Animals. Female mice were purchased and housed in the animal facilities of the University of Texas M. D. Anderson Cancer Center, Federal University of Sao Paulo, or University of Campinas. All animal procedures were approved by the respective IACUCs (Institutional Animal Care and Use Committee).

Human Specimens.

Incidental human melanoma samples were obtained, through written informed consent, from patients treated at the Surgery Branch of the National Cancer Institute (NCI) or at The University of Texas M. D. Anderson Cancer Center (MDACC).

Reagents.

Anti-MUC18 (mouse and human) antibodies were purchased from Santa Cruz Biotechnology and Zymed. Anti-bacteriophage (SIGMA); FITC-conjugated anti-human IgM, APC-conjugated anti-human CD5 and PE-conjugated anti-human MUC18 (BD Biosciences) were commercially obtained. MART-1 antibody was purchased from BioGenex and labeled with FITC by using EZ-label FITC protein labeling kit (Pierce) and Zeba desalt spin columns (Pierce). HRP-conjugated anti-rabbit, PE-conjugated anti-mouse (Pharmingen), Cy-3-conjugated anti-rabbit antibodies were purchased from Jackson ImmunoResearch Laboratories. Keyhole limpet hemocyanin (KLH)-conjugated peptide and synthetic peptide were synthesized and conjugated via the specifications (AnaSpec).

Cell culture and co-culture of B-1 lymphocytes and B16 melanoma cells. B16-derived melanoma cells (The Jackson Laboratory) were cultured in RPMI 1640 media (SIGMA) containing 10% of fetal bovine serum (FBS; Cultilab), antibiotics and supplements. Purified B-1 lymphocytes were obtained as described (Almeida et al., 2001). Only samples showing >95% purity were used.

Tumor Growth and Experimental Metastasis Assays.

The inventors used a standard model (e Brito et al., 2007; Popi et al., 2004) to deplete B-1 lymphocytes in mice. Untreated, radiated, or reconstituted cohorts of C57BL/6 mice received B16 cells intravenously ($10^5$ cells per mouse). Mice were sacrificed and the number of colonies on the surface of lungs determined on day 15 post administration. Primary tumor growth into the mouse footpad was measured daily.

Phage Display Screening and Binding Assays.

The inventors used a random phage library displaying the insert $CX_7C$(C, cysteine; X, any residue) for selection of peptides binding to melanoma cells post co-culture with B-1 lymphocytes (Giordano et al., 2001). As a pre-clearing step, $10^6$ B16 cells without exposure to B-1 lymphocytes were detached, washed and resuspended in RPMI containing 2% BSA plus $10^9$ transducing units (TU) of unselected phage library. Cells and phage were transferred to the top of a non-miscible organic lower phase (dibutyl phthalate: cyclohexane, 9:1 [v:v]) and centrifuged at 10,000 g for 10 min. The unbound phage population remaining in the aqueous upper phase (pre-cleared library) was collected into a fresh eppendorf tube and incubated with $10^6$ B16 cells isolated post co-culture with B-1 lymphocytes. Phage in the organic lower phase were recovered from the cell pellet by bacterial host infection (Pasqualini et al., 2000; Cardo-Vila et al., 2003; Marchio et al., 2004; Marchio et al., 2004; Kolonin et al., 2004; Arap et al, 2004; Hajitou et al., 2006).

For phage binding assays to B16 melanoma, $10^6$ cells pre and post co-culture with B-1 lymphocytes were incubated with each specific phage clone ($10^9$ TU) or negative controls. Melanoma cells and phage were centrifuged through the organic phase and the cell-bound phage clones were recovered by bacterial infection (Giordano et al., 2001).

Immunocapture Assays.

Immunocapture experiments were with anti-MUC18 or IgG control antibodies, as described (Pasqualini et al., 2000). ELISA with anti-IgG confirmed equal molar concentration of IgG on each of the wells. After blocking with PBS containing 3% BSA, 30 μg of protein from cell membrane extracts were added onto the wells for overnight incubation. Following washes, phage ($2 \times 10^9$ TU) were added to each well. Bound phage were recovered by bacterial infection.

In Vivo Phage Display.

Homing of phage to subcutaneous tumors was performed as described (Pasqualini and Ruoslahti, 1996). Animals received $1 \times 10^{10}$ TU of phage diluted in DMEM. Tumors and control organs were collected after 6 h of circulation. Bound phage were recovered by bacterial infection (Pasqualini and Ruoslahti, 1996).

Immunofluorescence and Flow Cytometry.

B16 melanoma cells pre- and post co-culture with B-1 lymphocytes were seeded in an 8-chamber slide (Nalge Nunc International) and incubated with phage ($10^9$ TU). Cells were washed, fixed and incubated with an anti-bacteriophage antibody followed by secondary antibody. For flow cytometry, melanoma cells or purified B-1 lymphocytes were incubated with primary antibody anti-MUC18 followed by PE-conjugated secondary antibody. To investigate the presence of B-1 lymphocytes in human melanoma samples, cells were isolated, washed, fixed and permeabilized with BD Cytofix/Cytoperm (BD Biosciences). Cells were stained either with isotype control or with specific antibody. Cells were analyzed with a FACS Calibur machine (BD Biosciences) equipped with Cell Quest software.

Immunofluorescence and Immunohistochemical Staining for MUC18 Detection in Tissue Specimens.

Tissue specimens were sectioned, mounted, and air-dried for 24 h. Antigen retrieval was performed with 0.1 M Citrate buffer (pH 6). Sections were stained with the UltraVision Plus Detection System, Anti-Polyvalent, HRP/AEC kit (LabVision Corp.) and counterstained with Gill's hematoxylin (SIGMA). For immunofluorescence, sections were washed, blocked and incubated with specific antibodies and Cy3-conjugated secondary antibodies.

Western Blot and Immunoprecipitation Assays.

Cells were lysed by using PBS containing 250 mM sucrose, 50 mM octylglucoside, 1 mM EDTA and protease inhibitors, resolved in a 4-20% gradient SDS-PAGE gel, transferred to nitrocellulose membranes and developed with the Enhanced Chemiluminescence (ECL) reagent (Amersham-Pharmacia). For detection of phosphorylated ERK1/2, total proteins were extracted as described (Perez et al., 2008)

RT-PCR.

RNA was purified by using the Perfect RNA® Mini kit extraction method (Eppendorf). First-strand cDNA synthesis was performed by using the Superscript II Reverse Transcriptase kit (Invitrogen). For the mouse MUC18 transcript amplification, the inventors used the primers 5'GGATCCTTGGCTTGCGCCCTCCGTCGG3' (SEQ ID NO:4) and 5'CTAATGCCTCAGATCGATGTATTTCTCTCC3' (SEQ ID NO:5) under the same conditions for template denaturation and elongation but with the annealing temperature of 60° C. As a loading control, the inventors used primers for the mouse glyceraldehyde 3'-phosphate dehydrogenase (GAPDH): 5'CGCCTGGTCACCAGGGCTGC3' (SEQ ID NO:6) and 5'CACCACCCTGTTGCTGTAGCC3' (SEQ ID NO:7).

Design of Small Hairpin RNA and Lentivirus Production.

Mouse MUC18 siRNA sequences 5' GGAGAGAAATACATCGATC 3' (SEQ ID NO:8) and 5'GATCGATGTATTTCTCTCC 3' (SEQ ID NO:9) were obtained from Dharmacon (On-Target Plus, NM_023061). Nonspecific control siRNA (nontargeting shRNA) sequences were 5'-TAAGGCTATGAAGAGATAC-3' (SEQ ID NO:10) and 5' GTATCTCTTCATAGCCTTA-3' (SEQ ID NO:11). shRNA sequences for both targeting and non-targeting were ligated into a lentiviral vector pLVTHM which drives the expression of the green fluorescent protein (GFP) (26) (a gift from Dr. Didier Trono, University of Geneva, Switzerland). The restriction enzymes Cla1 and Mlu1 were used. The lentiviruses were produced by infecting human embryonic kidney cells (293FT) with the sequence-verified pLVTHM, the packing plasmid (MD2G) and the envelope plasmid (PAX2), required for viral production. GFP-positive cells were enriched to 100% by fluorescence-activated cell sorting.

Statistical Analysis.

Graphical analyses (Balloon plots) were used to depict protein expression levels based on flow cytometry results. Spearman's rank correlation test was used to analyze the correlation between number of B-1 lymphocytes and MUC18 expression profile on patients. Statistical analysis of in vivo experiments was carried out by using Student's t-tests as indicated.

Results.

B-1 Lymphocytes Influence Malignant Melanoma Metastasis In Vivo.

The inventors first evaluated the role of B-1 lymphocytes in melanoma growth and metastasis in vivo, by selectively depleting the predominantly B-1 lymphocyte population from peritoneal and pleural surfaces of mice (Kantor and Herzenberg, 1993; Fagarasan et al., 2000; Almeida et al., 2001; Kantor, 1991). The inventors used external beam ionizing radiation to deplete B-1 lymphocytes with no detectable effect on other cell types (Brito et al., 2007; Popi et al., 2004). The inventors confirmed the depletion by flow cytometric analysis of cell surface markers: the inventors observed a severe reduction in the B-1 lymphocyte population (typically over 80% cell depletion) by using this procedure. Next, the inventors compared subcutaneous melanoma growth and experimental metastasis in radiated versus non-radiated (control) mice (FIG. 1A). In the radiated cohorts, the inventors observed tumor growth suppression (FIG. 1A—left panel) and marked reduction in melanoma metastasis (FIG. 1A—right panels). In either case, reconstitution with total peritoneal cells reverted tumor growth and metastasis to levels undistinguishable from those observed in control non-radiated mice. To evaluate which depleted cell population mediates this phenomenon, the inventors reconstituted radiated mice with either B-1 lymphocytes (FIG. 1B) or all other resident peritoneal cells but B-1 lymphocytes (FIG. 1C). It was shown that B-1 lymphocytes are necessary and sufficient to revert the radiation-induced metastasis suppression of melanoma. Finally, by using an unrelated genetic model of immunosuppression (X-linked immunodeficiency, Xid), the inventors also observed melanoma metastasis inhibition when mutant mice (constitutively B-1 lymphocyte-deficient (Khan et al., 1995; Santos-Lima et al., 2001)) were compared to their otherwise isogenic wild-type counterparts (FIG. 1D). These observations in Xid mutant mice are consistent with the results obtained from radiation-induced B-1 lymphocyte depletion. Together, these data from two independent experimental systems confirm that B-1 lymphocytes can control experimental metastasis derived from B16 melanoma cells.

Next, the inventors cultured melanoma cells either in a TRANSWELL Culture® system or with B-1 lymphocytes in co-culture. Surprisingly, co-culture enhanced melanoma metastasis. No effects on melanoma metastatic potential were observed when cells were cultured in shared media (Staquicini, 2004; Perez et al., 2008). Moreover, cell clusters forming between B16 melanoma cells and B-1 lymphocytes were observed by 48-72 hours of co-culture but not before; such heterotypic cell clusters contained one B16 melanoma cell plus five-to-ten B-1 lymphocytes. The inventors confirmed an intimate physical membrane interaction between the two cell types by transmission electron microscopy (Staquicini, 2004). In sum, these data show that a direct and "prolonged" (defined as ≧72 hours) cell-cell contact between B-1 lymphocytes and B16 melanoma cells renders the tumor cells more metastatic.

A MUC18-MUC18 Homophilic Interaction Mediates the Physical Contact Between Melanoma Cells and B-1 Lymphocytes.

Figure 2:
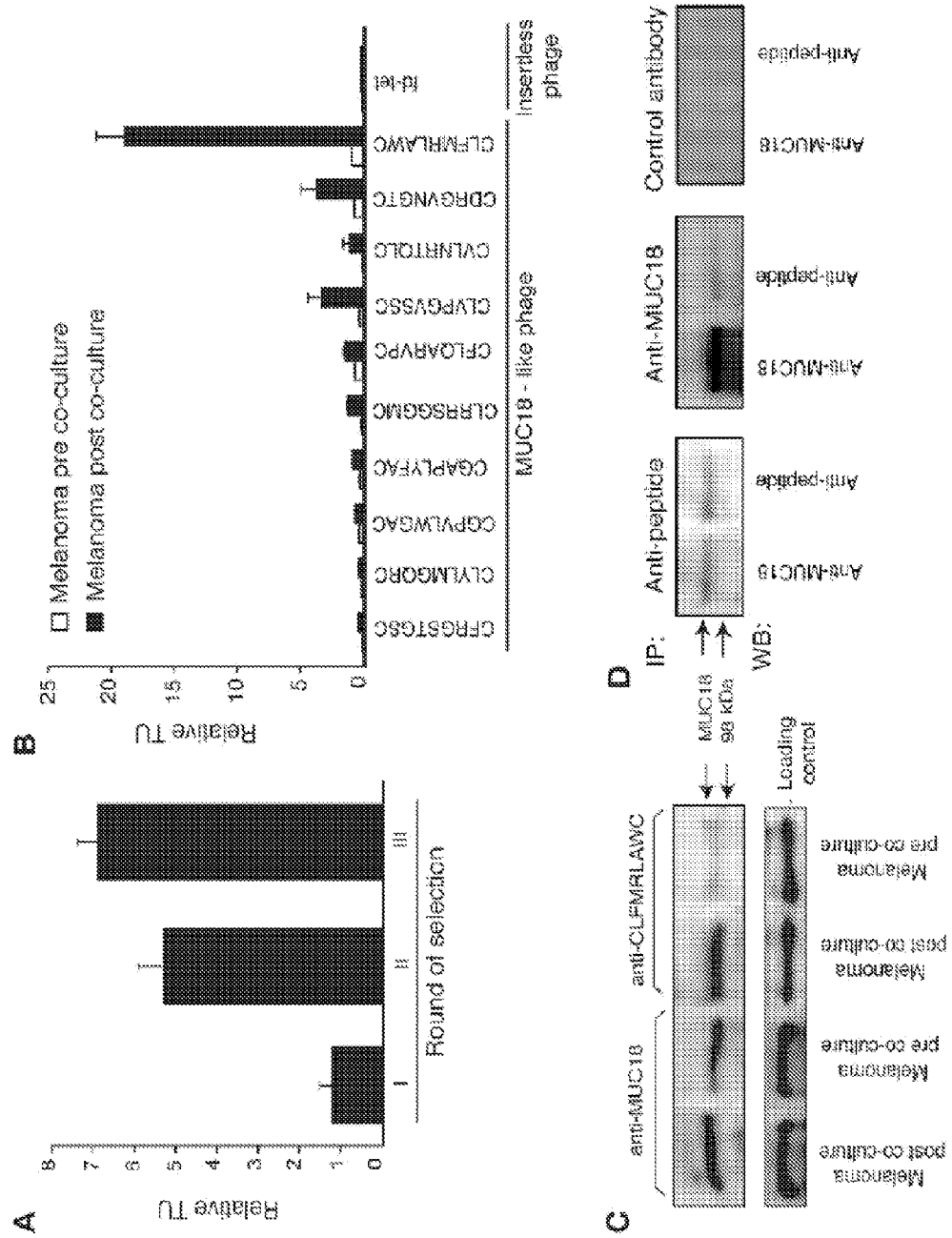

The inventors hypothesized that adhesion molecules expressed on B16 melanoma cell surfaces after contact with host B-1 lymphocytes would mediate the cell-cell interaction. In order to identify such molecules, the inventors used a phage display-based combinatorial approach (Giordano et al., 2001). The inventors designed a two-step aqueous-to-organic phase separation strategy to select ligands to melanoma cells with enhanced metastatic potential. First, the inventors pre-cleared the phage library on B16 melanoma cells prior to co-culture with B-1 lymphocytes. Next, the inventors selected the unbound bulk phage population (pre-cleared library) on isolated B16 melanoma cells after 72 hours of co-culture with B-1 lymphocytes and obtained strong serial enrichment (FIG. 2A). The inventors then proceeded to evaluate the binding of phage selected from the enriched population and found that 7 out of 10 individual clones tested (70%) preferentially bound to melanoma cells after co-culture with B-1 lymphocytes (range, 2- to 7-fold; median, 3-fold) relative to an insertless phage that served as negative control. Protein similarity searches revealed that several peptides displayed by the phage showing preferential binding to melanoma post co-culture were reminiscent of the sequence of the glycoprotein MUC18 (Shih, 1999; Yang et al., 2001).

The inventors then searched whether additional selected ligand peptides had homologous sequences to that protein. In total, the inventors found 48 motifs sharing sequence homology to the extracellular domain of MUC18. Of these, the inventors evaluated a panel of phage clones displaying peptides with homology to MUC18. The inventors found that 10 out of 15 individual clones (67%) bound preferentially to B16 melanoma cells post co-culture with B-1 lymphocytes (range, 2.5- to 20-fold; median 4-fold). In particular, phage displaying the cyclic peptide CLFMRLAWC which contains an embedded MUC18-like motif in reverse (sequence Arg-Met-Phe-Leu (SEQ ID NO:12) present in the extracellular portion of IgG1 domain; mouse MUC18 residues R114-L117) showed marked enrichment in phage binding relative to the negative control insertless phage (FIG. 2B). Sequences shown in FIG. 2B are as follows: CFRGSTGSC (SEQ ID NO:13); CLYLMGQRC (SEQ ID NO:14); CGPVLWGAC (SEQ ID NO:15); CGAPLYFAC (SEQ ID NO:16); CLRRSGGMC (SEQ ID NO:17); CFLQARVPC (SEQ ID NO:18); CLVPGVSSC (SEQ ID NO:19); CVLNRTQLC (SEQ ID NO:20); CDRGVNGTC (SEQ ID NO:21). The inventors then set out to functionally characterize the CLFMRLAWC-displaying phage and the corresponding homologous region within MUC18. The inventors developed antibodies against the melanoma-targeting CLFMRLAWC peptide to evaluate whether they recognize MUC18. Proteins from cell membrane extracts of melanoma cells co-cultured with or without B-1 lymphocytes were then probed with anti-MUC18 or anti-CLFMRLAWC peptide antibodies. Both antibodies against the native mouse MUC18 or against the CLFMRLAWC synthetic peptide detected undistinguishable protein bands by Western blot (FIG. 2C) suggesting that both recognize MUC18; reciprocal co-immunoprecipitation experiments were also consistent with such interpretation (FIG. 2D). Western blotting (FIG. 2C), immunofluorescence (FIG. 3A) and flow cytometry (FIG. 4B) analysis showed an increase in MUC18 expression in melanoma cells post co-culture with B-1 lymphocytes which directly correlated with the increase in MUC18-targeting.

Figure 3:
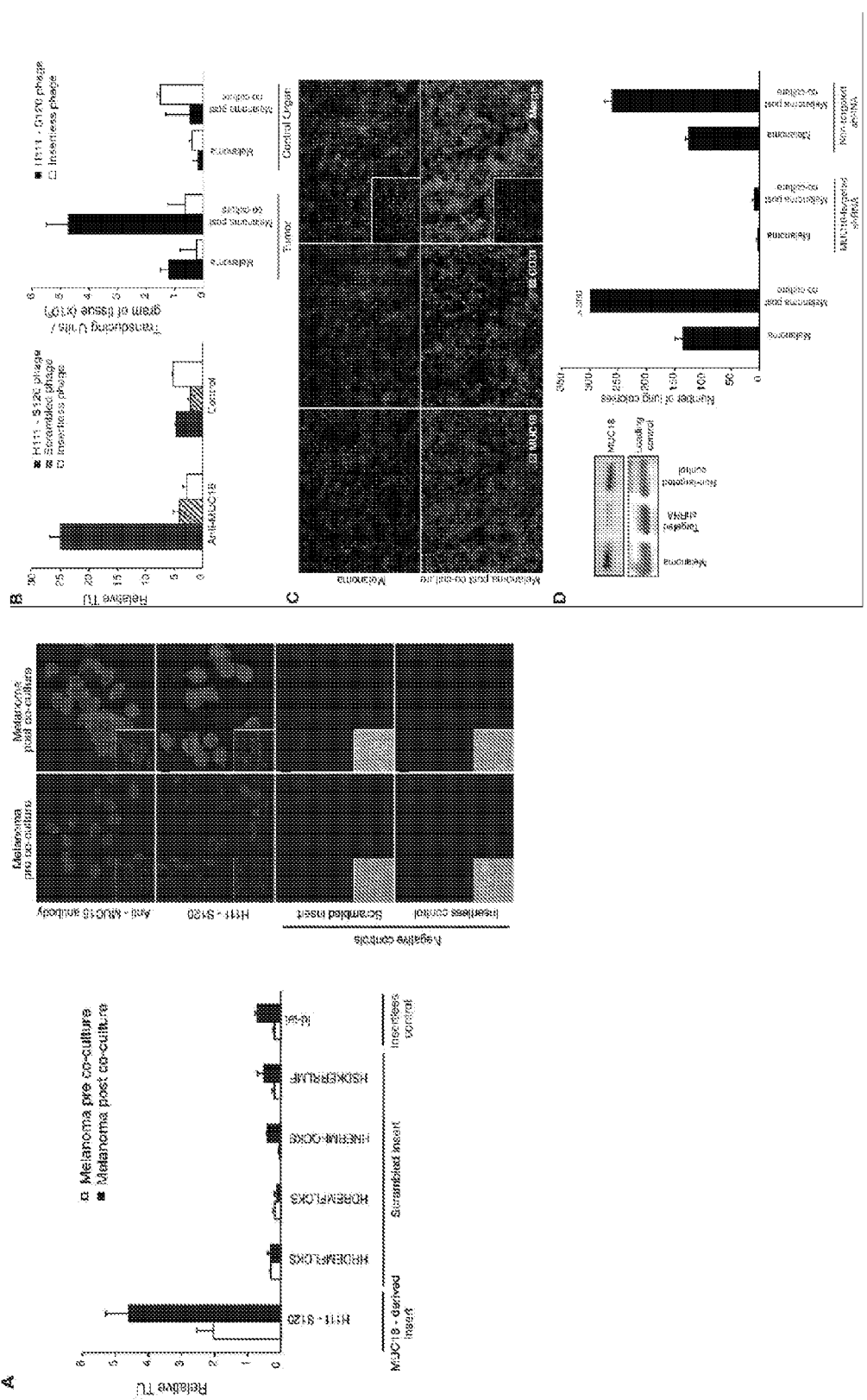
FIG. 3. MUC18-derived phage binds to MUC18. A, Binding of MUC18-derived phage on melanoma cells pre and post co-culture with B-1 lymphocytes. Left panel: a phage clone displaying a mouse MUC18-derived peptide (H111-S120) targets B16 malignant melanoma cells relative to insertless phage or phage clones displaying various scrambled versions of the MUC18-derived peptide. The Y axis is set forth in terms of relative transducing units ("Relative TU"). Right panel: immunostaining of melanoma cells with an anti-MUC18 antibody reveals a differential pattern of MUC18 expression on the cell surface. Staining with anti-phage antibody demonstrates that phage binding recapitulates the different levels of MUC18 expression pre and post co-culture with B-1 lymphocytes. B, Left panel: Specific binding of mouse MUC18-derived (H111-S120) phage to immunocaptured MUC18 relative to negative controls (insertless and scrambled peptide phage). The Y axis is set forth in terms of relative transducing units ("Relative TU"). Right panel: in vivo homing of MUC18-like phage to tumors before and after co-culture with B-1 lymphocytes. C, Double label immunofluorescence of tumors derived from melanoma cells before and after co-culture with B-1 lymphocytes. DAPI was used for nuclei staining D, Silencing of MUC18 expression in melanoma cells with small hairpin RNA. Decrease in protein expression was confirmed by immunoblotting. Co-culture of B-1 lymphocytes with MUC18-negative melanoma cells does not increase melanoma metastatic potential.

Based on the experiments described above, the inventors predicted that the native MUC18 protein sequence would recapitulate the phage binding mediated by the peptide CLFMRLAWC. To experimentally test such prediction, the inventors designed and constructed a phage clone displaying a peptide that encompass the corresponding native MUC18 protein sequence (residues H111-S120) for use in binding assays on melanoma cells pre and post co-culture with B-1 lymphocytes. Consistent with this hypothesis, the inventors observed that the display of a MUC18-derived (H111-S120) peptide sequence on phage promotes preferential binding to the surface of B16 melanoma cells after co-culture with B-1 lymphocytes (2.5-fold relative to the baseline binding to malignant melanoma cells pre co-culture with B-1 lymphocytes); in contrast, several negative controls (a series of phage clones engineered to display scrambled versions of the peptide insert) had their binding to melanoma cells abolished to background levels regardless of co-culture with B-1 lymphocytes (FIG. 3A—left panel). Moreover, to evaluate whether MUC18 might indeed be responsible for the differential phage binding, the inventors compared the magnitude of phage binding to cell membrane expression of that molecule (FIG. 3A—right panel). The inventors observed (i) that MUC18 expression increases after co-culture with B-1 lymphocytes and (ii) that there is a direct correlation between targeted phage binding and cell surface expression of MUC18 relative to controls. Together, these data not only show that a MUC18-derived ligand peptide mediates binding to B16 melanoma cells but also establish the overexpression of the cell surface receptor MUC18 itself in the melanoma cells after B-1 lymphocyte co-culture.

To confirm that the H111-S120 peptide can functionally behave as MUC18 in the phage context as well, the inventors evaluated the binding of H111-S120 phage to immunocaptured MUC18. The inventors show that H111-S120 phage but not negative controls (including insertless or scrambled insert phage) bind to immunocaptured MUC18; no binding was observed when immunocapture was carried out by using an irrelevant IgG isotype control (FIG. 3B—left panel). It was also observed that anti-MUC18 antibodies specifically inhibit phage binding mediated by the MUC18-derived peptide H111-S120 relative to controls. Furthermore, to study the specificity of the MUC18 targeted-phage in vivo, the inventors evaluated phage homing in mice subcutaneously implanted with melanoma cells before and after co-culture with B-1 lymphocytes (FIG. 3B). The inventors observed marked binding of MUC18 targeted-phage to tumors derived from melanoma post co-culture with B-1 lymphocytes compared to melanoma and control organ (FIG. 3B—right panel). Phage binding is accompanied by increased expression of MUC18 in tumors from melanoma co-cultured with B-1 lymphocytes (FIG. 3C).

Next, the inventors used shRNA to silence the expression of MUC18 in melanoma cells and to determine whether presence of MUC18 on the cell surface is required for the biological phenomenon to occur. Decrease in expression of MUC18 was confirmed by immunoblotting (FIG. 3D). MUC18-depleted cells were co-cultured with B-1 lymphocytes for 72 h and injected intravenously into mice. The inventors used B16 and B16 transduced with non-targeting shRNA as controls. As previously observed, co-culture of MUC18-expressing melanoma cells (parental B16 or B16 transduced with non-targeting shRNA) with B-1 lymphocytes increases melanoma metastasis. However, such pro-metastatic effect is abrogated when MUC18-negative cells are used, a result consistent with the hypothesis that a MUC18-MUC18-mediated cell interaction renders melanoma cells more metastatic. Furthermore, a marked decrease in the number of lung colonies was observed in animals inoculated with MUC18-negative cells, again supporting the importance of this molecule in metastasis.

Taken together, these results confirm the specificity of the interaction and support the concept that a MUC18-MUC18 homophilic interaction mediates the physical contact between B16 cells and B-1 lymphocytes. To gain insight into the molecular basis of such interaction, the inventors generated a panel of phage to combine alanine scanning site-directed mutagenesis and binding assays. Compared to wild-type H111-S120 phage, the inventors identified four key residues (Arg114, Cys118, Lys119, and Ser120) in MUC18 whose mutation abolished phage binding to melanoma cells regardless of co-culture with B-1 lymphocytes. Results of these mutational studies again indicate binding specificity.

B-1 Lymphocytes Express MUC18.

Figure 4:
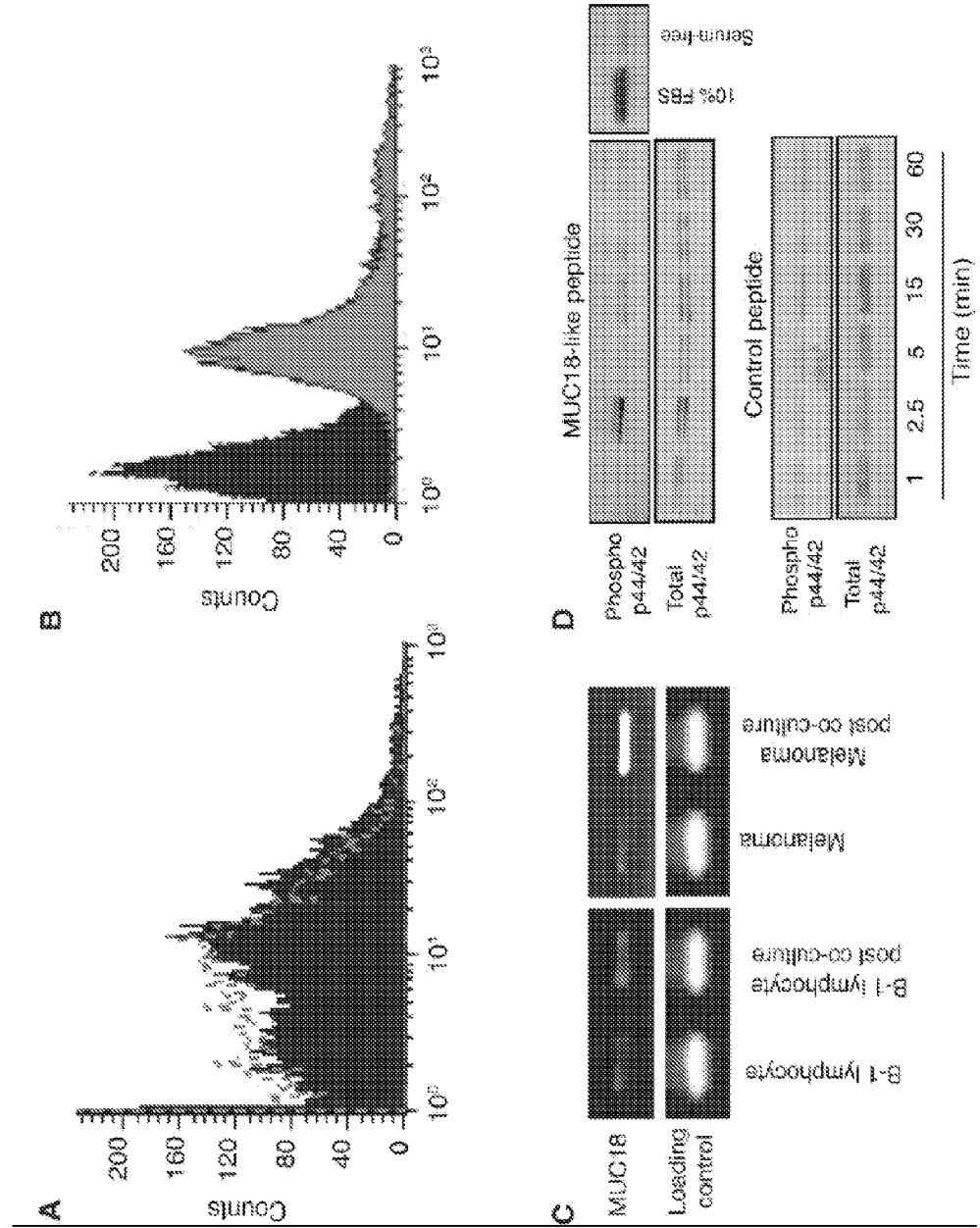
FIG. 4. A and B, FACS analysis shows that B-1 lymphocytes express high levels of cell surface MUC18. In contrast to B16 melanoma cells (B), the inventors observed lack of MUC18 up-regulation on B-1 lymphocytes after co-culture with malignant melanoma cells. (A) The black histogram represents B-1 lymphocytes. The gray dotted line histogram represents B-1 lymphocytes after co-culture with B16 malignant melanoma cells. (B) The gray histogram represents B16 malignant melanoma cells after co-culture with B-1 lymphocytes. A ~7-fold enhancement in MUC18 cell surface expression is detected after co-culture with B-1 lymphocytes. C, MUC18 expression in B-1 lymphocytes by RT-PCR analysis. No differences in expression levels of the MUC18 transcript were observed in B-1 lymphocytes co-cultured with melanoma cells (left panel). In contrast, the inventors clearly detected increased expression of MUC18 in melanoma cells post co-culture with B-1 lymphocytes (right panel). D, Cell signaling through MAPK pathways. Phosphorylation of ERK1/2 was investigated by immunoblotting in different time points after melanoma cell activation. The inventors observed specific phosphorylation of p44/42 after 2.5 min of cell stimulation with MUC18-like peptide (upper panel). Control unrelated peptide showed no effect in protein phosphorylation (lower panel). Total p44/42 served as the loading control.

Given that phage selected to mimic a ligand expressed on the surface of B-1 lymphocytes resembled MUC18 and bound specifically to MUC18 on the surface of melanoma cells, the inventors evaluated whether B-1 lymphocytes would also express MUC18 on their own cell surfaces as well. Flow cytometric analysis revealed cell surface expression of MUC18 in B-1 lymphocytes (FIG. 4A). However, in contrast to the MUC18 overexpression clearly observed in B16 melanoma cells post co-culture with B-1 lymphocytes (FIG. 4B), no change in MUC18 expression was detected on the cell surfaces of B-1 lymphocytes themselves after co-culture. The inventors next used RT-PCR analysis to confirm changes in MUC18 expression after cell-cell contact. Consistent with the previous findings, the inventors again observed an upregulation of MUC18 transcripts in melanoma cells (but not in B-1 lymphocytes) post co-culture (FIG. 4C), suggesting that MUC18 transcriptional control is differentially regulated in each cell type. Indeed, binding of B-1 lymphocytes to melanoma cells in vitro induce activation of the MAP kinase signaling pathway only in melanoma cells, while ERK1/2 phosphorylation appears to be constitutive in B-1 lymphocytes (Perez et al., 2008). Thus, in order to further investigate the role of MUC18 in this cell-cell interaction, the inventors evaluated the effect of MUC18-like peptide in the activation of the MAP kinase pathway in melanoma cells. Cells were treated with MUC18-like synthetic peptide and protein phosphorylation was analyzed by immunoblotting (FIG. 4D). The inventors show phosphorylation of ERK1/2 at 2.5 min after cell activation. In contrast, an unrelated control peptide did not induce ERK1/2 phosphorylation. Collectively, these data suggest (i) that MUC18 is expressed in both cell types but differentially regulated and (ii) that a homophilic MUC18-MUC18 ligand-receptor system on the cell surface of B16 melanoma cells and B-1 lymphocytes mediates a heterotypic cell-cell interaction that ultimately leads to ERK1/2 phosphorylation and increase in melanoma metastasis.

A Potential Functional Role for B-1 Lymphocytes in Human Malignant Melanoma.

Figure 5:
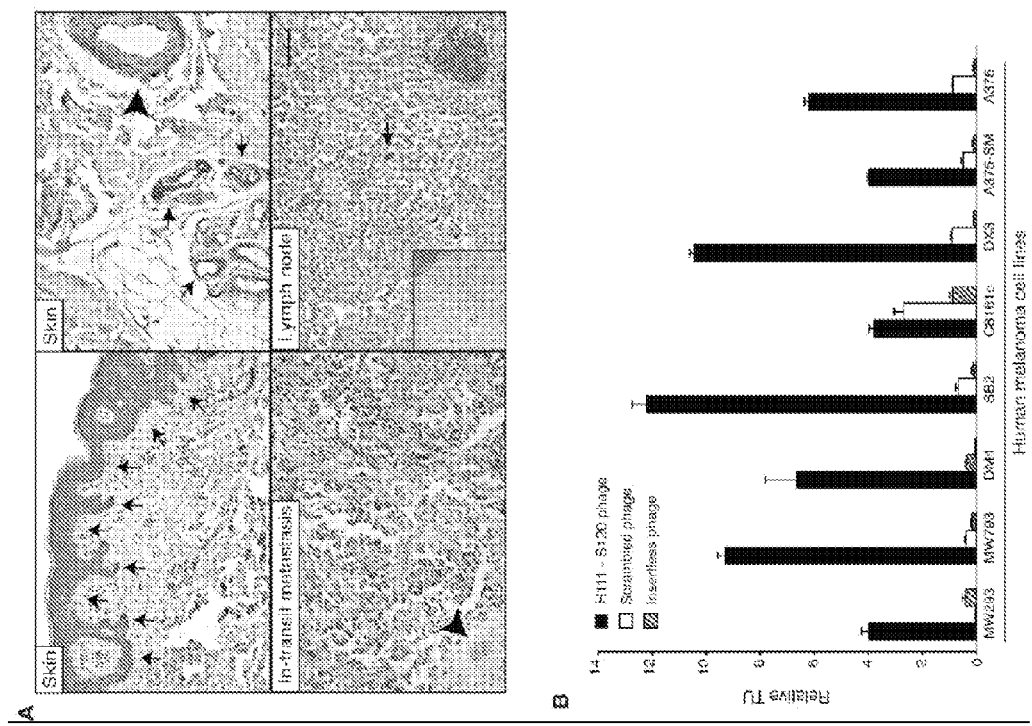
FIG. 5. Expression of MUC18 in human melanoma. A, Samples of skin, in transit and lymph node metastases were immunostained with anti-human MUC18 antibody. Arrows point to MUC18-expressing melanoma cells in the epidermis (top left), dermis and exocrine ducts (top right) and lymph node metastases (bottom right). Arrowhead point to MUC18 positive melanoma cells in vascular endothelial cells (top right and bottom left) (100-fold magnification). Negative control is shown in inset, bottom-right panel. B, Phage binding assay to human melanoma cell lines. A scrambled version of the peptide and insertless phage were used as negative control. The Y axis is set forth in terms of relative transducing units ("Relative TU").

To investigate the relevance of these findings in human disease, the inventors first evaluated the expression of MUC18 in patient-derived melanoma primary tumors and metastases: immunohistochemical analysis of MUC18 expression in skin, "in-transit", and in lymph nodes (FIG. 5A) showed marked MUC18 expression in both melanoma cells and vascular endothelial cells, consistent with other descriptive reports (Jean et al., 1998; Luca et al., 1993). Of note, only melanoma cells but not lymphocytes stained positive for MUC18 within lymph nodes, a result again consistent with the observation that B-1 lymphocytes are the only MUC18-expressing B cells in both mice and humans. Moreover, the inventors also examined the binding capacity of the MUC18-targeted phage to a panel of 8 well-established human melanoma cell lines (FIG. 5B). The inventors observed specific binding of the H111-S120 phage to all cell lines relative to negative controls.

Figure 6:
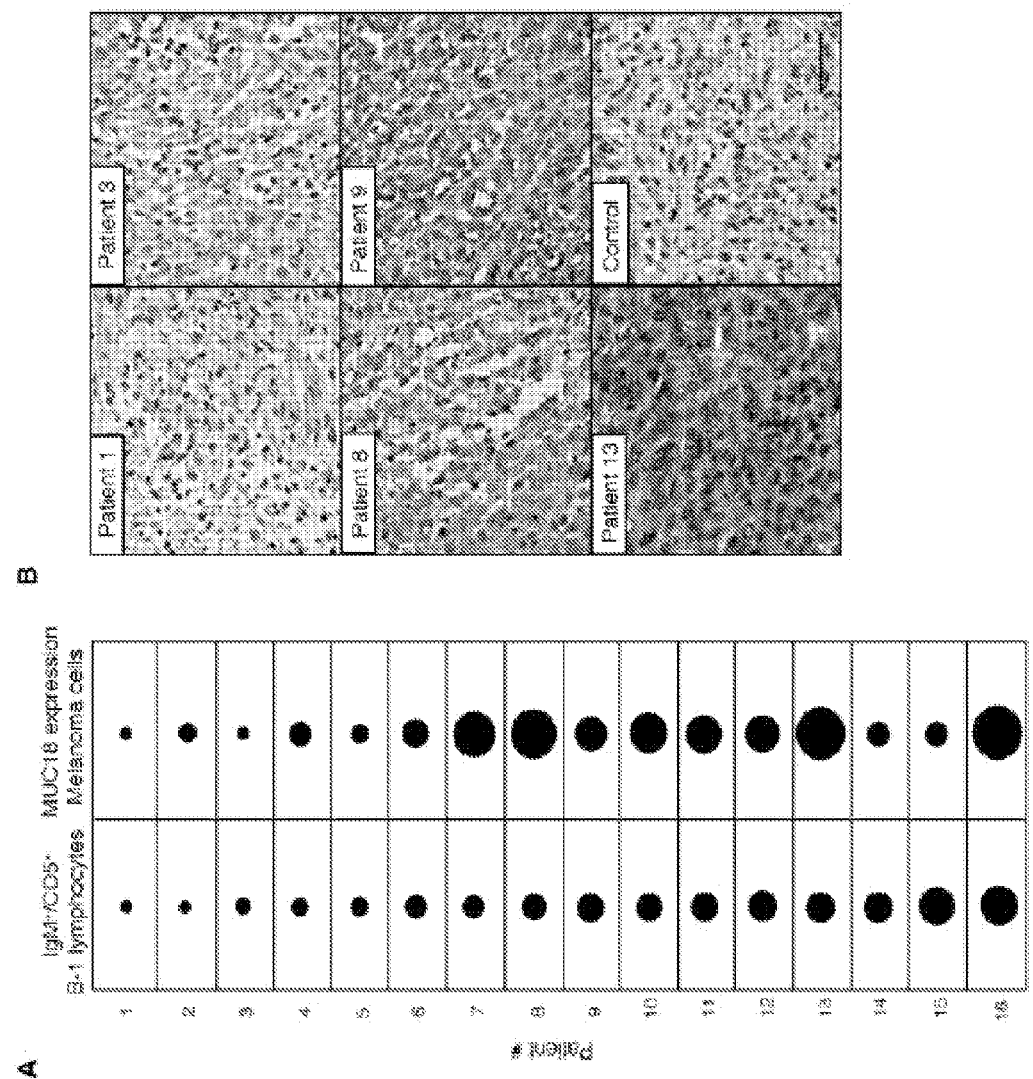
FIG. 6. Correlation between number of B-1 lymphocytes and MUC18 expression in human melanoma. A, Flow cytometric analysis of melanoma samples is graphically represented as a balloon plot. A positive correlation is observed between increasing number of B-1 lymphocytes within the tumors and increasing expression of MUC18 on melanoma cells. B, Histological analysis of representative samples stained for MUC18 (20-fold magnification).

Next, the inventors asked (i) whether the human counterpart (34, 35) of murine B-1 lymphocytes (heretofore termed "human B-1 lymphocytes") are present in sites of human melanoma metastasis and (ii) whether this B cell population would recapitulate the functional behavior of mouse B-1 lymphocytes in the context of malignant melanoma. The inventors used flow cytometric analysis to evaluate patient-derived samples (obtained from surgically removed metastatic melanoma cases; n=16) for the presence of human B-1 lymphocytes (FIG. 6A). B-1 cells were distinguished among other lymphocytes by CD5/IgM double-expression while human MUC18-expressing tumor cells were identified within MART-1+ melanoma cells. Expression of surface markers was graphically represented as a "balloon plot" (FIG. 6A). The inventors observed a direct correlation between increasing number of human B-1 lymphocytes within the tumors and increasing expression of MUC18 on melanoma cells (r=0.6, p<0.05). Histological analysis of representative melanomas with mild (Patients #1 and 3), moderate (Patients #8 and 9), and marked (Patient #13) levels of MUC18 expression on melanoma cells illustrates differential expression of the protein (FIG. 6B). Together, these results establish that human B-1 lymphocytes are present in melanoma metastases and that such presence accounts for increased expression of MUC18 in human melanoma cells. As such, the MUC18 homophilic mechanism of heterotypic cell interaction appears clearly preserved across species and it is likely functional in human melanoma as well.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,472,509
U.S. Pat. No. 4,472,509
U.S. Pat. No. 5,021,236
U.S. Pat. No. 5,206,347
U.S. Pat. No. 5,401,511
U.S. Pat. No. 5,603,872
U.S. Pat. No. 5,889,155
Almeida et al., *Int. Immunol.*, 13:1193-201, 2001.
Arap et al., *Cancer Cell*, 6:275-84, 2004.
Arap et al., *Curr. Opin. Oncol.*, 10:560-565, 1998.
Arap et al., *Science*, 279:377-380, 1998.
Baichwal and Sugden, In: *Gene Transfer*, Kucherlapati (Ed.), Plenum Press, NY, 117-148, 1986.
Bakhshi et al., *Cell*, 41(3):899-906, 1985.
Barany and Merrifield, In: *The Peptides*, Gross and Meienhofer (Eds.), Academic Press, NY, 1-284, 1979.
Bartholomaeus et al., *J. Natl. Cancer Inst.*, 53:1065-72, 1974.
Berland and Words, *Annu. Rev. Immunol.*, 20:253-300, 2002.
Cardó-Vila et al., *Mol. Cell*, 11:1151-62, 2003.
Chen and Okayama, *Mol. Cell. Biol.*, 7(8):2745-2752, 1987.
Cleary and Sklar, *Proc. Natl. Acad. Sci. USA*, 82(21):7439-7443, 1985.
Coffin, In: *Virology*, Fields et al. (Eds.), Raven Press, NY, 1437-1500, 1990.
Coupar et al., *Gene*, 68:1-10, 1988.
Coussens and Werb, *Nature*, 420:860-7, 2002.
de Visser et al., *Cancer Cell*, 7:411-23, 2005.
e Brito et al., *Lupus*, 16:947-54, 2007.
Eliceiri and Cheresh, *Curr. Opin. Cell. Biol.*, 13:563-568, 2001.
Ellerby et al. *Nature Med.*, 9:1032-1038, 1999.
Fagarasan et al., *Immunol. Rev.*, 76:205-15, 2000.
Fidler and Gersten, In: *Neoplasm Immunity: Experimental and Clinical*, Crispen (Ed.), Amsterdam: Elsevier Holland, 3:3-15, 1980.
Fidler, In: Cancer: Principles & Practice of Oncology, Vincent et al. (Eds.), NY, Lippincott-Raven, 1:135-52, 1997.
Folkman, *In: Cancer: Principles and Practice*, eds. DeVita et al., 3075-3085, Lippincott-Raven, NY, 1997.
Friedmann, *Science*, 244:1275-1281, 1989.
Giordano et al., *Nat. Med.*, 7:1249-53, 2001.
Gomez-Foix et al., *J. Biol. Chem.*, 267:25129-25134, 1992.
Goodman & Gilman's "The Pharmacological Basis of Therapeutics"
Gopal, *Mol. Cell. Biol.*, 5:1188-1190, 1985.
Graham and Prevec, In: *Methods in Molecular Biology: Gene Transfer and Expression Protocol*, Murray (Ed.), Humana Press, Clifton, N.J., 7:109-128, 1991.
Graham and Van Der Eb, *Virology*, 52:456-467, 1973.
Graham et al., *J. Gen. Virl.*, 36(1):59-74, 1977.
Grunhaus and Horwitz, *Seminar in Virology*, 3:237-252, 1992.
Hajitou et al., *Cell*, 125:385-98, 2006.
Hardy et al., *Immunol. Rev.*, 93:53-79, 1986.
Harlow and Lane, In: *Antibodies: A Laboratory Manual*, Cold Spring Harbor Laboratory, 1988.
Hendrix, *Current Biol.*, 9:914-917, 1999.
Hermonat and Muzycska, *Proc. Natl. Acad. Sci. USA*, 81:6466-6470, 1984.
Herz and Gerard, *Proc. Natl. Acad. Sci. USA*, 90:2812-2816, 1993.
Horwich et al. *J. Virol.*, 64:642-650, 1990.
Jean et al., *J. Biol. Chem.*, 273:16501-8, 1998.
Johnson et al., In: *Biotechnology And Pharmacy*, Pezzuto et al. (Eds.), Chapman and Hall, NY, 1993.
Jones and Shenk, *Cell*, 13:181-188, 1978.
Kantor, *Immunol. Today*, 12:389-91, 1991.
Kantorand Herzenberg, *Annu. Rev. Immunol.*, 11:501-38, 1993.
Kerr et al., *Br. J. Cancer*, 26(4):239-257, 1972.
Khan et al., *Immunity*, 3:283-99, 1995.
Kolonin et al., *Nat. Med.*, 10:625-32, 2004.
Le Gal La Salle et al., *Science*, 259:988-990, 1993.
Levrero et al., *Gene*, 101:195-202, 1991.
Luca et al., *Melanoma Res.*, 3:35-41, 1993.
Mann et al., *Cell*, 33:153-159, 1983.
Marchio et al., *Cancer Cell*, 5:151-62, 2004.
Merrifield, *Science*, 232(4748):341-347, 1986.
Nicolas and Rubinstein, In: *Vectors: A survey of molecular cloning vectors and their uses*, Rodriguez and Denhardt, eds., Stoneham: Butterworth, pp. 494-513, 1988.
Nicolau et al., *Methods Enzymol.*, 149:157-176, 1987.
Paskind et al., *Virology*, 67:242-248, 1975.
Pasqualini and Ruoslahti, *Nature*, 380:364-6, 1996.
Pasqualini et al., *Cancer Res.*, 60:722-27, 2000.

Pérez et al., *Cancer Sci.*, 99:920-8, 2008.
Physicians Desk Reference
Popi et al., *Immunology*, 113:348-54, 2004.
Potter et al., *Proc. Natl. Acad. Sci. USA*, 81:7161-7165, 1984.
Prehn, *J. Reticuloendothel. Soc.*, 10:1-16, 1971.
Prehn, *Science*, 176:170-171, 1972.
Racher et al., *Biotechnology Techniques*, 9:169-174, 1995.
Ragot et al., *Nature*, 361:647-650, 1993.
Remington: The Science and Practice of Pharmacy," 20th edition, Gennaro, Lippincott, 2000
Rich et al., *Hum. Gene Ther.*, 4:461-476, 1993.
Ridgeway, In: *Vectors: A Survey of Molecular Cloning Vectors and Their Uses*, Rodriguez et al. (Eds.), Stoneham: Butterworth, 467-492, 1988.
Rippe, et al., *Mol. Cell. Biol.*, 10:689-695, 1990.
Rosenfeld et al., *Cell*, 68:143-155, 1992.
Rosenfeld et al., *Science*, 252:431-434, 1991.
Santos-Lima et al., *Eur. J. Immunol.*, 31:634-45, 2001.
Shih, *J. Pathol.*, 189:4-11, 1999.
Staquicini, FI. *B-1 lymphocytes modulate the metastatic potential of murine melanoma through a specific interaction mediated by MUC18*, disseration Ph.D., Federal University of Sao Paulo, 2004.
Stewart and Young, In: *Solid Phase Peptide Synthesis*, 2d. ed., Pierce Chemical Co., 1984.
Stratford-Perricaudet and Perricaudet, In: *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1990.
Tam et al., *J. Am. Chem. Soc.*, 105:6442, 1983.
Temin, In: *Gene Transfer*, Kucherlapati (Ed.), NY, Plenum Press, 149-188, 1986.
Tsujimoto et al., *Nature*, 315:340-343, 1985.
Tur-Kaspa et al., *Mol. Cell. Biol.*, 6:716-718, 1986.
Wexler et al., *Cancer*, 37:1701-1706, 1976.
Wong et al., *Gene*, 10:87-94, 1980.
Wu and Wu, *Biochemistry*, 27: 887-892, 1988.
Wu and Wu, *J. Biol. Chem.*, 262:4429-4432, 1987.
Yang et al., *Gene*, 265:133-45, 2001.

---

The invention claimed is:

1. A method of treating melanoma or leukemia comprising administering to a subject having melanoma or leukemia a peptide comprising the sequence of SEQ ID NO:22, SEQ ID NO:1 or SEQ ID NO:2, wherein if the peptide comprises SEQ ID NO:2, then the peptide is not full-length melanoma cell adhesion molecule 18 (MUC 18).

2. The method of claim 1, wherein the cancer is leukemia.

3. The method of claim 1, wherein the cancer is melanoma.

4. The method of claim 1, wherein the peptide is SEQ ID NO:22.

5. The method of claim 1, wherein the subject is a mammal.

6. The method of claim 5, wherein the mammal is a human.

7. The method of claim 6, comprising administering the peptide in a pharmaceutically acceptable carrier.

8. The method of claim 1, further comprising administering a second therapeutic agent to the subject.

9. The method of claim 1, wherein the peptide is coupled to a therapeutic agent.

10. The method of claim 9, wherein the therapeutic agent is a drug, a chemotherapeutic agent, a radioisotope, a pro-apoptosis agent, an anti-angiogenic agent, a hormone, a cytokine, a cytotoxic agent, a cytocidal agent, a cytostatic agent, a peptide, a protein, an antibiotic, an antibody, a Fab fragment of an antibody, a hormone antagonist, a nucleic acid or an antigen.

11. The method of claim 10, wherein the anti-angiogenic agent is selected from the group consisting of thrombospondin, angiostatin, pigment epithelium-derived factor, angiotensin, laminin peptides, fibronectin peptides, plasminogen activator inhibitors, tissue metalloproteinase inhibitors, interferons, interleukin 12, platelet factor 4, interferon gamma-induced protein 10 (IP-10), growth-regulated protein beta (Gro-β), 2-methoxyoestradiol, proliferin-related protein, carboxiamidotriazole, CM101 endotoxin, Marimastat, pentosan polysulphate, angiopoietin 2, interferon-alpha, herbimycin A, (7,7-(carbonyl-bis[imino-N-methyl-4,2-pyrrolecarbonylimino[N-methyl-4,2-pyrrole]-carbonylimino])-bis-(1,3-naphthalene disulfonate)) (PNU145156E), 16K prolactin fragment, Linomide, thalidomide, pentoxifylline, genistein, endostatin, paclitaxel, Docetaxel, polyamines, a proteasome inhibitor, a kinase inhibitor, a signaling peptide, accutin, cidofovir, vincristine, bleomycin, (3R,4S,5S,6R)-5-methoxy-4-[(2R,3R)-2-methyl-3-(3-methyl-2-butenyl)-oxiranyl]-1-oxaspiro[2,5]oct-6-yl(chloroacetyl)carbamate 5-methoxy-4-(2-methyl-3-(3-methyl-2-butenyl)-1-oxaspiro(2,5)oct-6-yl (chloroacetyl) carbamate O-(chloroacetylcarbamoyl) fumagillol (AGM-1470), platelet factor 4 and minocycline.

12. The method of claim 10, wherein the pro-apoptosis agent is selected from the group consisting of 4'-demethyl-epipodophyllotoxin 9-[4,6-O—(R)-ethylidene-beta-D-glucopyranoside], 4'-dihydrogen phosphate, ceramide sphingomyelin, Bax, Bid, Bik, Bad, caspase-3, caspase 8, caspase-9, fas, fas ligand, fadd, fap-1, tradd, faf, rip, reaper, apoptin, interleukin-2 converting enzyme or annexin V.

13. The method of claim 10, wherein the cytokine is selected from the group consisting of interleukin 1 (IL-1), IL-2, IL-5, IL-10, IL-12, IL-18, interferon-γ (IF-γ), IF-α, IF-β, tumor necrosis factor-α (TNF-α), or GM-CSF (granulocyte macrophage colony stimulating factor).

14. The method of claim 1, wherein the peptide is SEQ ID NO:1.

15. The method of claim 1, wherein the peptide is SEQ ID NO:2.

\* \* \* \* \*